United States Patent
Kim et al.

(10) Patent No.: US 12,226,395 B2
(45) Date of Patent: Feb. 18, 2025

(54) COMPOSITION FOR PREVENTING OR TREATING NEURODEGENERATIVE DISEASES, CONTAINING DITERPENE-BASED COMPOUND

(71) Applicant: KOREA RESEARCH INSTITUTE OF BIOSCIENCE AND BIOTECHNOLOGY, Daejeon (KR)

(72) Inventors: Won Gon Kim, Daejeon (KR); Baek Soo Han, Daejeon (KR); Jeong Su Byun, Daejeon (KR); Van Minh Nguyen, Daejeon (KR); Ha Young Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 17/811,327

(22) Filed: Jul. 8, 2022

(65) Prior Publication Data

US 2022/0370407 A1    Nov. 24, 2022

Related U.S. Application Data

(62) Division of application No. 16/763,630, filed as application No. PCT/KR2018/013990 on Nov. 15, 2018, now abandoned.

(30) Foreign Application Priority Data

Nov. 15, 2017 (KR) .................... 10-2017-0152487
Nov. 15, 2017 (KR) .................... 10-2017-0153861

(51) Int. Cl.
*A61K 31/36* (2006.01)
*A23L 33/105* (2016.01)
*A61K 31/232* (2006.01)

(52) U.S. Cl.
CPC ............ *A61K 31/36* (2013.01); *A23L 33/105* (2016.08); *A61K 31/232* (2013.01)

(58) Field of Classification Search
CPC ....... A61K 31/36; A61K 36/83; A23L 33/105; A61P 25/28; A61P 25/16
See application file for complete search history.

(56) References Cited

U.S. PATENT DOCUMENTS 6,187,756 B1    2/2001  Lee et al.
9,034,916 B2 *  5/2015  Kim ................... A61P 25/28
                                                      514/715

(Continued)

FOREIGN PATENT DOCUMENTS

CN    104507466    4/2015
EP    0457295      11/1991

(Continued)

OTHER PUBLICATIONS

KR20120113924A (translation provided by Google Patents). (Year: 2012).*

(Continued)

*Primary Examiner* — Matthew P Coughlin
*Assistant Examiner* — Ashli Ariana Chicks
(74) *Attorney, Agent, or Firm* — Vorys, Sater, Seymour and Pease LLP; Mih Suhn Koh

(57) ABSTRACT

The present invention relates to a pharmaceutical composition for preventing or treating neurodegenerative diseases comprising a diterpene, or a pharmaceutically acceptable salt thereof. Specifically, the diterpene of the present invention can prevent or treat neurodegenerative diseases caused by inhibition of Nurr1 activity by activating Nurr1 and inhibiting the inflammatory response.

5 Claims, 3 Drawing Sheets

Specification includes a Sequence Listing.

(56) References Cited

U.S. PATENT DOCUMENTS

| | | | | |
|---|---|---|---|---|
| 10,792,323 | B2* | 10/2020 | Kim | A61P 25/16 |
| 11,738,063 | B2* | 8/2023 | Kim | A61K 31/36 424/778 |
| 2014/0142173 | A1 | 5/2014 | Kim et al. | |

FOREIGN PATENT DOCUMENTS

| | | |
|---|---|---|
| JP | 2010-241727 A | 10/2010 |
| WO | 2012138034 | 10/2012 |
| WO | 2013110006 | 7/2013 |

OTHER PUBLICATIONS

Li, et al., Helvetica Chimica Acta, 93:1172. (Year: 2010).*

Chen, et al., Phytomed., 21:82. (Year: 2013).*

JP2010241727A (translation provided by Google Patents) (Year: 2010).*

Jacobsen, J. S. et al., "The Release of Alzheimer's Disease B-Amyloid Peptide is Reduced by Phorbol Treatment", The Journal of Bilogical Chemistry, 1994, vol. 269, No. 11, pp. 8376-8382.

Han, B.S, et al., "Daphnane Diterpenes from Daphne Genkwa Activate Nurr1 and Have a Neuroprotective Effect in an Animal Model of Parkinson's Disease", Journal of Natural Product, 2016, vol. 79, No. 6, pp. 1604-1609.

Wu Zhihai "Phytochemical investigation on the diterpenes from the roots of Daphne genkwa and anthocyanins from the fruits of *Lycium ruthenicum* Murr.", Chinese Master's Theses Full-text Database / Medicine and Health Sciences (ISSN 1674-0246) (Mar. 2016) pp. E057-74.

Chen et al., "Toxicity of daphnane-type diterpenoids from Genkwa Flos and their pharmacokinetic profile in rat", Phytomedicine, 8 pages, 2013.

Li et al., "Daphnane-Type Diterpenoids from the Flower Buds of Daphne genkwa", Helvetica Chimica Acta, 2010, vol. 93, pp. 1172-1179.

Office Action issued in corresponding Vietnamese Application 1-2020-03209, issued on Aug. 9, 2024, 3 pages.

* cited by examiner

[Fig. 1A]
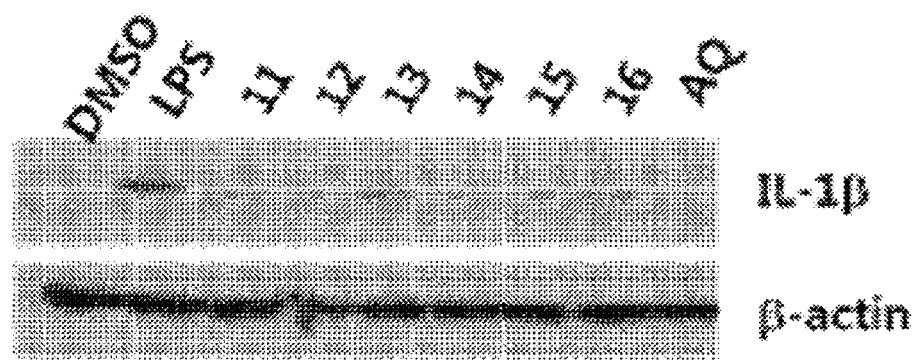
[Fig. 1B]
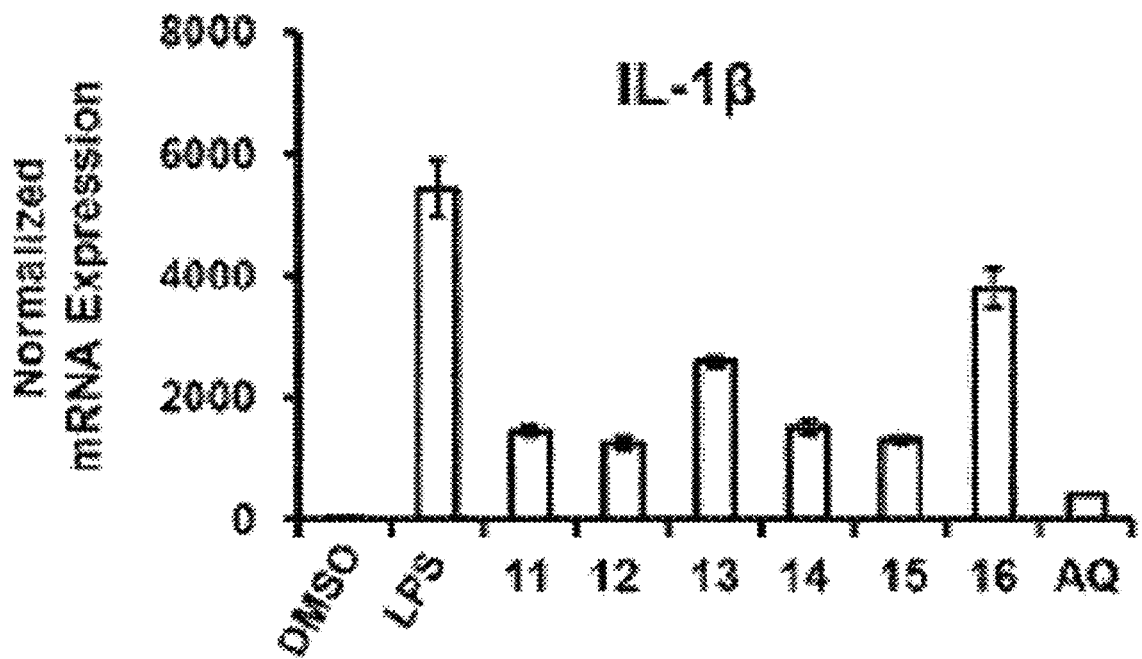

[Fig. 1C]
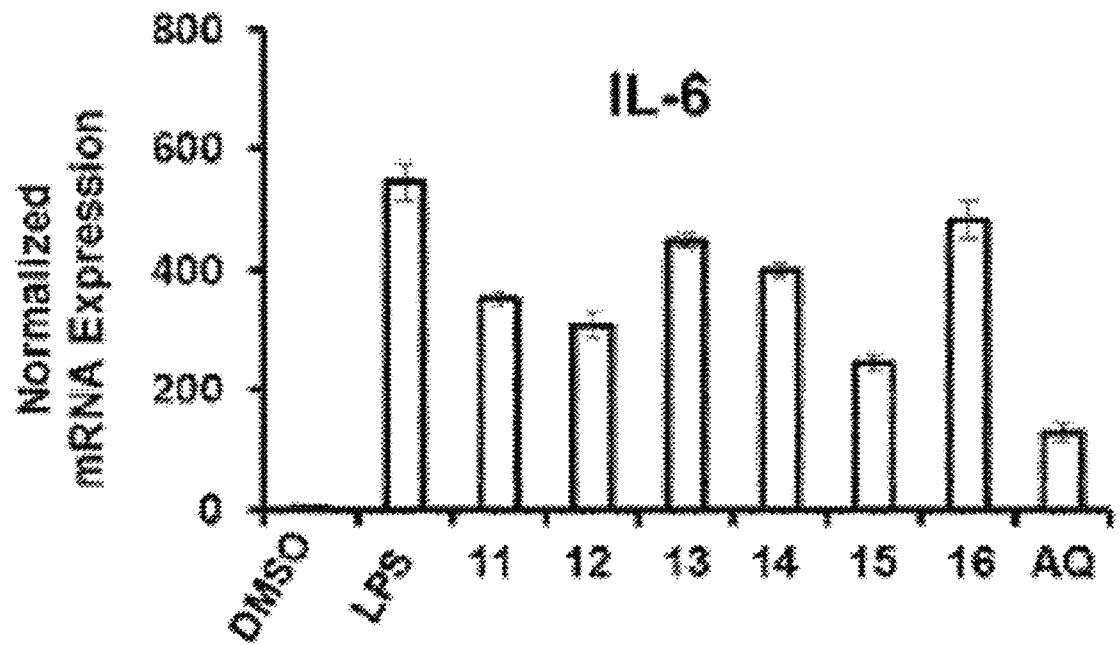
[Fig. 1D]
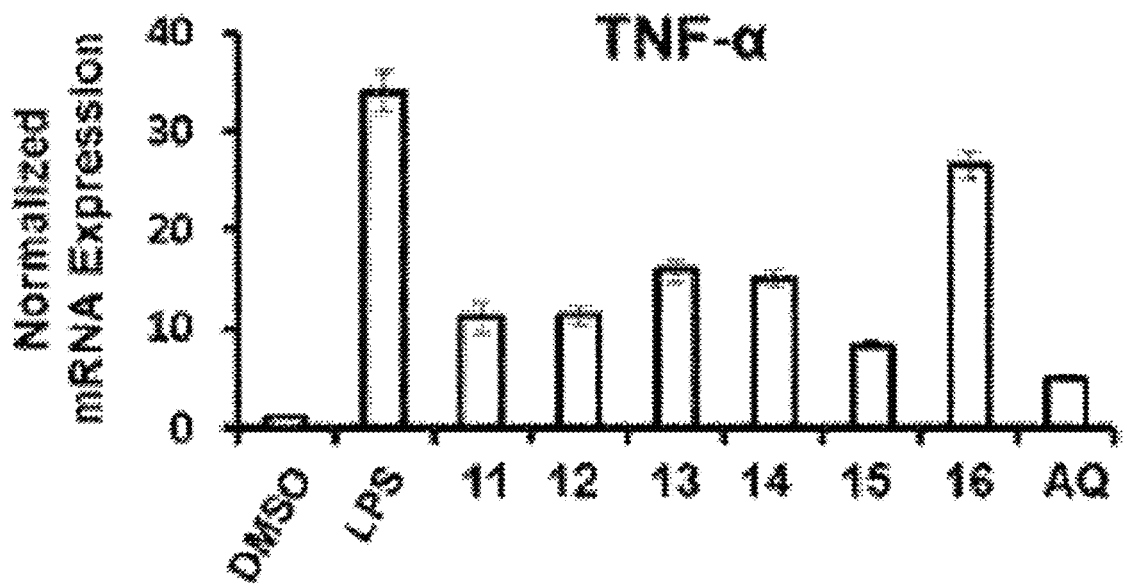

[Fig. 2]
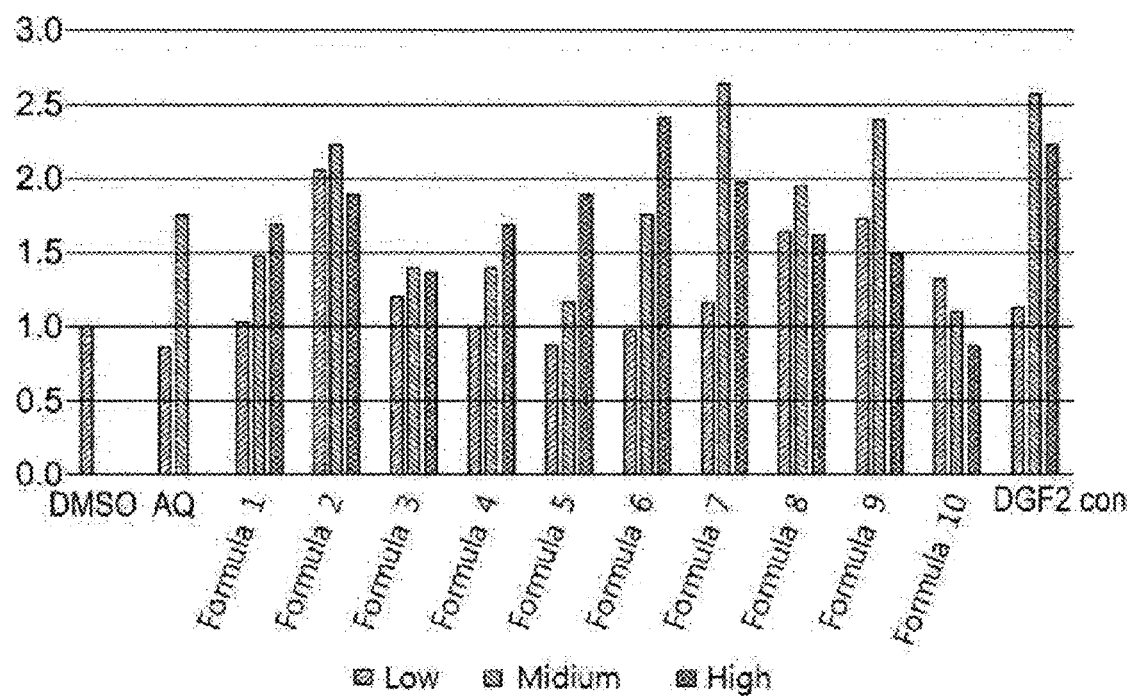

SEQUENCE LISTING

```
Sequence total quantity: 1
SEQ ID NO: 1           moltype = DNA   length = 19
FEATURE                Location/Qualifiers
misc_feature           1..19
                       note = GLA4 binding gene
source                 1..19
                       mol_type = other DNA
                       organism = synthetic construct
SEQUENCE: 1
ctcggaggac agtactccg                                              19
```

COMPOSITION FOR PREVENTING OR TREATING NEURODEGENERATIVE DISEASES, CONTAINING DITERPENE-BASED COMPOUND

BACKGROUND

Technical Field

The present invention relates to a pharmaceutical composition for preventing or treating neurodegenerative diseases comprising a diterpene, or a pharmaceutically acceptable salt thereof.

In addition, the present invention relates to a health functional food for preventing or improving neurodegenerative diseases comprising a diterpene, or a pharmaceutically acceptable salt thereof.

Background Art

As various bio-regulatory functions of natural physiologically active substances separated from natural substances are known, research in fields such as development of new drugs using natural physiologically active substances and health functional food has been actively conducted. However, natural products contain a wide variety of physiologically active substances, but the physical and chemical properties of each substance are different, so even if the same natural product is extracted as a target, the kinds of bioactive substances that are separated according to the type of extraction solvent are different. In addition, even if the physiologically active substance is separated from the same natural product, it has been reported that there are different characteristics of the activity and its effect depending on the type. Therefore, recently, studies have been actively conducted to separate new and unknown bioactive substances by different extraction solvents for the same natural product.

Neurodegenerative diseases are associated with symptoms in which neurons degrade, lose function, and often die. Patients with neurodegenerative diseases may experience severe degeneration in cognitive or motor abilities, and as these diseases are predominantly progressive, their quality of life and expectations for life may be significantly reduced as a result.

These diseases include Parkinson's Disease (PD), Alzheimer's disease (AD), amyotrophic lateral sclerosis (ALS), Huntington's disease (HD), Frontotemporal Dementia, Cortico Basal Degeneration, progressive supranuclear palsy (PSP) and other diseases.

Meanwhile, a significant number of neurodegenerative diseases are significantly related to Nurr1. Specifically, US Patent Publication No. 2009-0226401 discloses that Parkinson's disease, a type of neurodegenerative disease, is a disease associated with dopaminergic neurons, and discloses a therapeutic effect of Parkinson's disease when Nurr1 is activated. Also, International Patent Publication No. WO2010-04221 discloses that Nurr1 plays an essential role in activating dopamine, and a method of treating Parkinson's disease by regulating the neurotransmission that activates Nurr1 and activates dopamine.

The representative neurodegenerative disease caused by dysfunction of Nurr1 is Parkinson's disease. Parkinson's disease is one of the major diseases in modern aging society, which is characterized by tremor, stiffness, bradykinesia, and gait abnormality, and is a chronic disease caused by a lack of neurotransmitters called dopamine in the substantia nigra and corpus striatum of the brain.

Known drugs for treating Parkinson's disease include L-dopa drugs, dopamine receptor agonists, anti-cholinergic drugs, Eldepryl, etc. Most of these drugs do not provide causal treatment of Parkinson's disease, but act to control conditions, and thus need to be administered continually, Although many medicines have been produced and commercialized for the treatment of Parkinson's disease so far, an essential therapeutic agent for completely treating Parkinson's disease has not yet been developed.

Thus, the present inventors confirmed that the compounds obtained by using various extraction and fractionation solvents from the flowers, stems and roots of *Daphne genkwa* activate Nurr1 and suppress the inflammatory reaction, confirming that the therapeutic effect is excellent for various neurodegenerative diseases including Parkinson's disease caused by Nurr1 dysfunction and completed the present invention.

The present invention refers to the contents of the invention of US Patent Publication No. 2009-0226401 and International Patent Publication No. WO2010-04221.

DETAILED DESCRIPTION OF THE INVENTION

Technical Problem

The object of the present invention is to provide a pharmaceutical composition for preventing or treating neurodegenerative diseases comprising a diterpene, or a pharmaceutically acceptable salt thereof.

Also, the present invention is to provide a health functional food for preventing or improving neurodegenerative diseases comprising a diterpene, or a pharmaceutically acceptable salt thereof.

Technical Solution

The present invention is a pharmaceutical composition for the prevention or treatment of neurodegenerative diseases comprising a diterpene, or a pharmaceutically acceptable salt thereof as an embodiment, wherein the diterpene provides a pharmaceutical composition for preventing or treating of neurodegenerative diseases using at least one selected from the group comprising Formulas 1 to 16 below.

Or the present invention provides a pharmaceutical composition for the prevention or treatment of neurodegenerative diseases using at least one selected from the group comprising a compound represented by Formula A as an active ingredient The diterpene of the present invention is a compound represented by the following Formulas 1 to 16, specifically yuanhuafine (Formula 1), genkwadaphnine (Formula 2), genkwanine H (Formula 3), genkwanine M (Formula 4), genkwanin K (Formula) 5), yuanhuapine (Formula 6), genkwanin A (Formula 7), orthobenzoate 2 (Formula 8), 1,2α-dihydrodaphnetoxin (Formula 9) or genkwanin I (Formula 10), acutilonine F (Formula 11), wikstroemia factor M1 (Formula 12), yuanhuadine (Formula 13), yuanhuatine (Formula 14), prostratin Q (Formula 15) or 12-O-n-deca-2,4,6-trienoyl-phorbol-(13)-acetate (Formula 16).

[Formula 1]
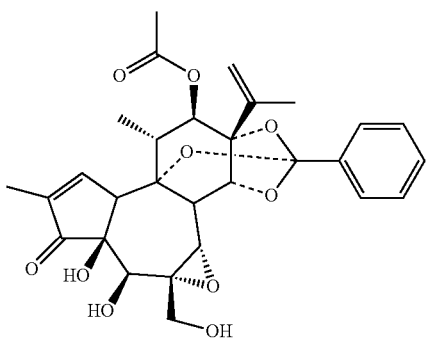
[Formula 2]
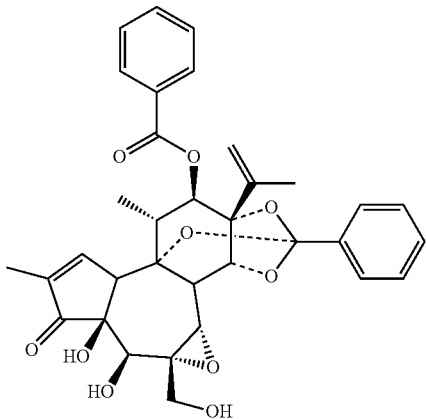
[Formula 3]
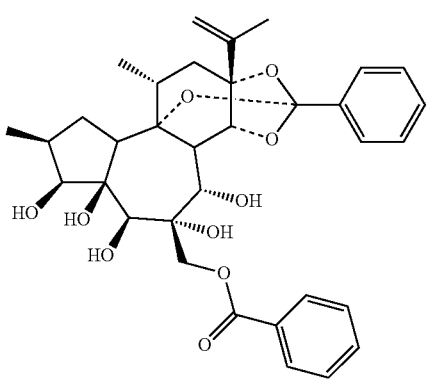
[Formula 4]
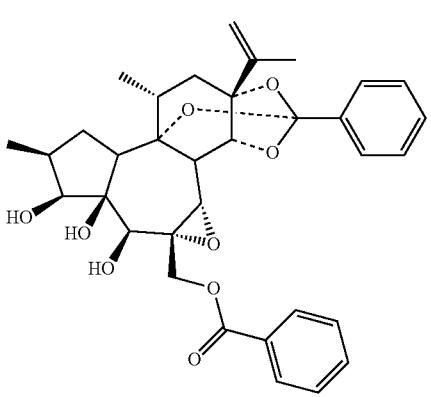
[Formula 5]
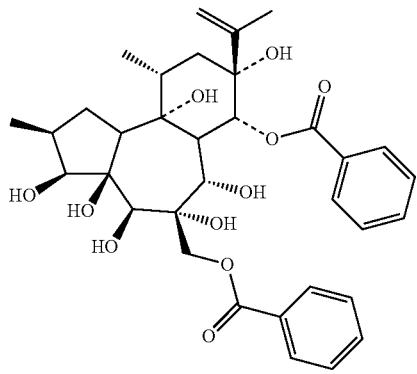
[Formula 6]
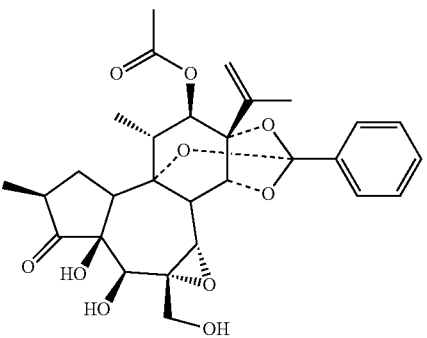
[Formula 7]
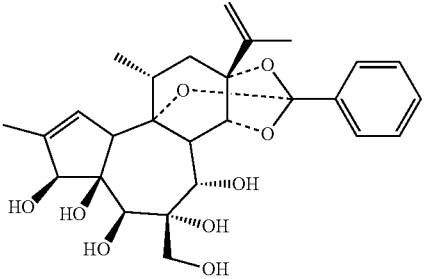
[Formula 8]
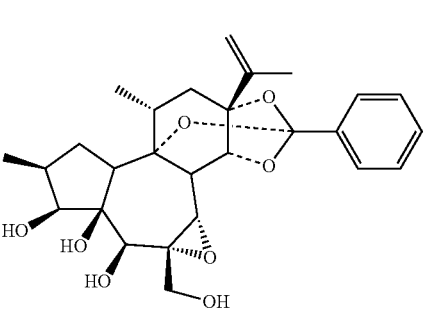
[Formula 9]
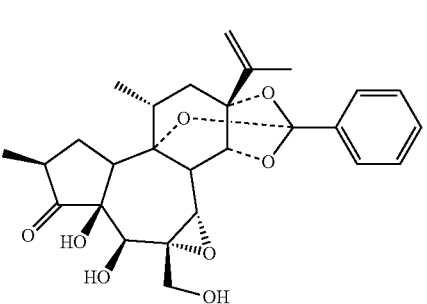

[Formula 10]

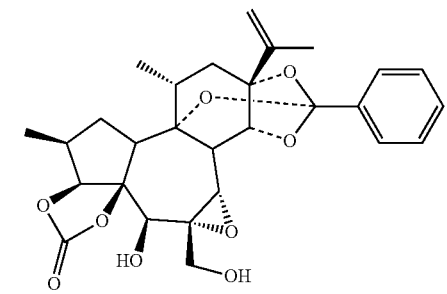

[Formula 11]

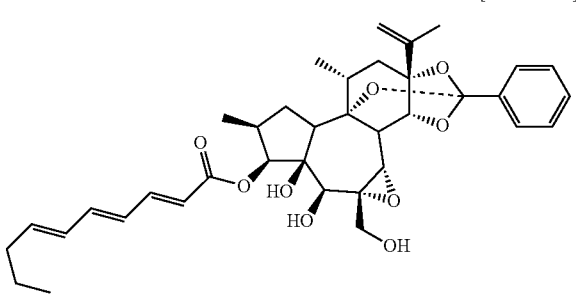

[Formula 12]

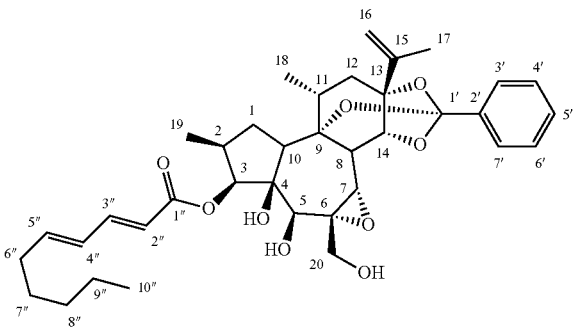

[Formula 13]

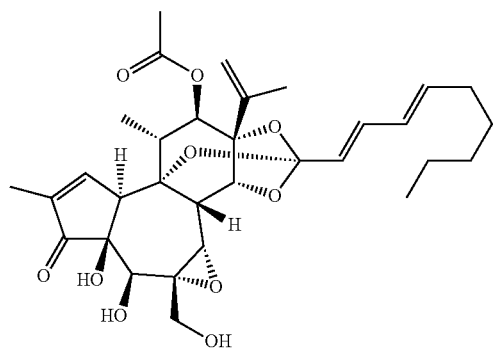

[Formula 14]

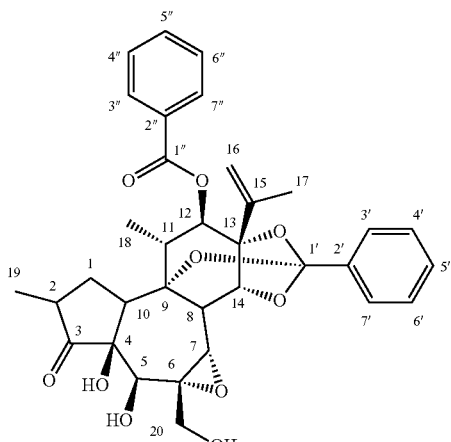

[Formula 15]

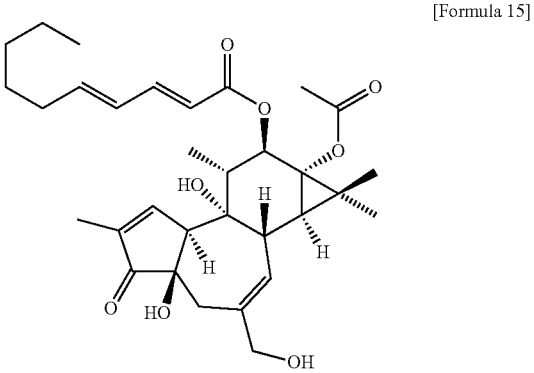

[Formula 16]

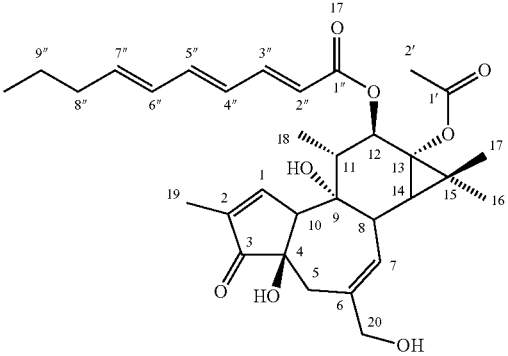

The compound of Formula 1, yuanhuafine, is named the IUPAC name of (2S,3aR,3cS,4aR,5S,5aS,8bR,9R,10R,10aS)-5,5a-dihydroxy-4a-(hydroxymethyl)-7, 9-dimethyl-6-oxo-2-phenyl-10a-(prop-1-en-2-yl)-3a,3b,3c,4a,5,5a,8a,9,10,10a-decahydro-6H-2,8b-epoxyoxireno[2'',3'':6',7']azuleno[5',4':3,4]benzo[1,2-d][1,3]dioxol-10-yl acetate, and The compound of Formula 2, genkwadaphnine, is named the IUPAC name of (2S,3aR,3cS,4aR,5S,5aS,8bR,9R,10R,10aS)-5,5a-dihydroxy-4a-(hydroxymethyl)-7,9-dimethyl-6-oxo-2-phenyl-10a-(prop-1-en-2-yl)-3a,3b,3c,4a,5,5a,8a,9,10,10a-decahydro-6H-2,8b-epoxyoxireno[2'',3'':6',7']azuleno[5',4':3,4]benzo[1,2-d][1,3]dioxol-10-yl benzoate, and The compound of Formula 3, genkwanine H is named the IUPAC name of ((2S,3aR,4S,5S,6S,6aR,7S,8S,9bR,10R,11aR)-4,5,6,6a,7-pentahydroxy-8,10-dimethyl-2-phenyl- 11a-(prop-1-en-2-yl)dodecahydro-5H-2,9b-epoxyazuleno[5',4':3,4]benzo[1,2-d][1,3]dioxol-5-yl)methyl benzoate, and The compound of Formula 4, genkwanine M is named the IUPAC name of ((2S,3aR,3cS,4aR,5S,5aR,6S,7S,8bR,9R,10aR)-5,5a,6-trihydroxy-7,9-dimethyl-2-phenyl-10a-(prop-1-en-2-yl)dodecahydro-4aH-2,8b-epoxyoxireno[2",3":6',7']azuleno[5',4':3,4]benzo[1,2-d][1,3]dioxol-4a-yl)methyl benzoate, and The compound of Formula 5, genkwanin K is named the IUPAC name of ((2S,3S,3aR,4S,5S,6S,7R,8R,10R,10aR)-7-(benzoyloxy)-3,3a,4,5,6,8,10a-heptahydroxy-2,10-dimethyl-8-(prop-1-en-2-yl)tetradecahydrobenzo[e]azulen-5-yl)methyl benzoate, and The compound of Formula 6, yuanhuapine is named the IUPAC name of (2S,3aR,3cS,4aR,5S,5aS,7S,8bR,9R,10R,10aS)-5,5a-dihydroxy-4a-(hydroxymethyl)-7,9-dimethyl-6-oxo-2-phenyl-10a-(prop-1-en-2-yl)dodecahydro-6H-2,8b-epoxyoxireno[2",3":6',7']azuleno[5',4':3,4]benzo[1,2-d][1,3]dioxol-10-yl acetate, and The compound of Formula 7, genkwanin A is named the IUPAC name of (2S,3aR,4S,5S,6S,6aR,7S,9bR,10R,11aR)-5-(hydroxymethyl)-8,10-dimethyl-2-phenyl-11a-(prop-1-en-2-yl)-3a,3b,4,5,6,7,9a,10,11,11a-decahydro-6aH-2,9b-epoxyazuleno[5',4':3,4]benzo[1,2-d][1,3]dioxole-4,5,6,6a,7-pentaol, and The compound of Formula 8, orthobenzoate 2 is named the IUPAC name of (2S,3aR,3cS,4aR,5S,5aR,6S,7S,8bR,9R,10aR)-4a-(hydroxymethyl)-7,9-dimethyl-2-phenyl-10a-(prop-1-en-2-yl)dodecahydro-5aH-2,8b-epoxyoxireno[2",3":6',7']azuleno[5',4':3,4]benzo[1,2-d][1,3]dioxole-5,5a,6-triol, and The compound of Formula 9, 1, 2α-dihydrodaphnetoxin is named the IUPAC name of (2S,3aR,3cS,4aR,5S,5aS,7S,8bR,9R,10aR)-5,5a-dihydroxy-4a-(hydroxymethyl)-7,9-dimethyl-2-phenyl-10a-(prop-1-en-2-yl)dodecahydro-6H-2,8b-epoxyoxireno[2",3":6',7']azuleno[5',4':3,4]benzo[1,2-d][1,3]dioxol-6-one.

and The compound of Formula 11, acutilonine F is named the IUPAC name of (2S,3aR,3cS,4aR,5S,5aS,6S,7S,8bR,9R,10aR)-5,5a-dihydroxy-4a-(hydroxymethyl)-7,9-dimethyl-2-phenyl-10a-(prop-1-en-2-yl)dodecahydro-6H-2,8b-epoxyoxireno[2",3":6',7']azuleno[5',4':3,4]benzo[1,2-d][1,3]dioxol-6-yl (2E,4E,6E)-deca-2,4,6-trienoate, and The compound of Formula 12, wikstroemia factor M1 is named the IUPAC name of (2S,3aR,3cS,4aR,5S,5aS,6S,7S,8bR,9R,10aR)-5,5a-dihydroxy-4a-(hydroxymethyl)-7,9-dimethyl-2-phenyl-10a-(prop-1-en-2-yl)dodecahydro-6H-2,8b-epoxyoxireno[2",3":6',7']azuleno[5',4':3,4]benzo[1,2-d][1,3]dioxol-6-yl (2E,4E)-deca-2,4-dienoate, and The compound of Formula 13, yuanhuadine is named the IUPAC name of (2S,3aR,3cS,4aR,5S,5aS,8bR,9R,10R,10aS)-5,5a-dihydroxy-4a-(hydroxymethyl)-7,9-dimethyl-6-oxo-2-phenyl-10a-(prop-1-en-2-yl) dodecahydro-6H-2,8b-epoxyoxireno [2",3": 6',7']azuleno[5',4': 3,4]benzo[1,2-d][1,3]dioxol-10-yl benzoate, and The compound of Formula 14, yuanhuatine is named the IUPAC name of (1aR,1bS,4aR,7aS,7bS,8R,9R,9aS)-9a-acetoxy-4a,7b-dihydroxy-3-(hydroxymethyl)-1,1,6,8-tetramethyl-5-oxo-1a,1b,4,4a,5,7a,7b,8,9,9a-decahydro-1H-cyclopropa[3,4]benzo[1,2-e]azulen-9-yl (2E,4E)-deca-2,4-dienoate and The compound of Formula 15, prostratin Q is named the IUPAC name of (2S,3aR,3bS,3cS,4aR,5S,5aS,8aR,8bR,9R,10R, 10aS)-5,5a-dihydroxy-4a-(hydroxymethyl)-7,9-dimethyl-2-((1E,3E)-nona-1,3-dien-1-yl)-6-oxo-10a-(prop-1-en-2-yl)-3a,3b,3c,4a,5,5a,8a,9,10,10a-decahydro-6H-2,8b-epoxyoxireno[2",3":6',7']azuleno[5',4':3,4]benzo[1,2-d][1,3]dioxol-10-yl acetate, and The compound of Formula 16, 12-O-n-deca-2,4,6-trienoyl-phorbol-(13)-acetate is named the IUPAC name of (4aR,7bS,8R,9R,9aS)-9a-acetoxy-4a,7b-dihydroxy-3-(hydroxymethyl)-1,1,6,8-tetramethyl-5-oxo-1a,1b,4,4a,5,7a,7b,8,9,9a-decahydro-1H-cyclopropa[3,4]benzo[1,2-e]azulen-9-yl (2E,4E,6E)-deca-2,4,6-trienoate The diterpene may be prepared by a method known to those skilled in the art, or may be prepared by purchasing or synthesizing a commercially available compound, and may be separated and purified from a plant known in the art using a polar or non-polar solvent. Specifically, the compound can be extracted and separated from the red beans. More specifically, the compound can be separated from the extract of flower, stem, root of Daphne genkwa.

As used herein, the term "Daphne genkwa" refers to a deciduous shrub of dicotyledonous Myrtales thymelaeaceae, and is also called lilac daphne. It grows mainly on the seashore.

The extract of Daphne genkwa the present invention means an extract obtained from the flowers, stems and roots of Daphne genkwa. Specifically, the extract may be an extract obtained by extracting the flowers, stems and/or roots of Daphne genkwa with water or an organic solvent, more specifically, it may be an extract obtained by extraction with water, C1 to C5 lower alkyl alcohol or a mixed solvent thereof. The alkyl alcohol may be 10%, 20%, 30%, 40%, 50%, 60%, 70%, 80%, 90% or 100% alkyl alcohol.

The extract of Daphne genkwa according to an embodiment of the present invention is preferably an extract extracted with 80% ethanol.

The extract of Daphne genkwa may be a fraction of the extract, wherein the fraction refers to an active fraction obtained by fractionating the compound of the present invention from the extract of Daphne genkwa using a specific solvent.

According to an embodiment of the present invention, the obtained extract of Daphne genkwa is obtained by separating the fractional layer of each solvent using an organic solvent such as hexane, chloroform, ethyl acetate, butanol or distilled water or a mixed solvent thereof, and the compounds of the present invention can be separated and purified to high purity using a separation method known in the art, such as chromatography, to produce a fraction.

The pharmaceutical composition of the present invention may be used in the form of any one or more compounds selected from the group containing the compounds of Formulas 1 to 16 or a pharmaceutically acceptable salt thereof.

As used herein, the term "pharmaceutically acceptable salt" refers to any salt that retains the desired biological and/or physiological activity of the compound, and the undesirable toxicological effect is minimal. As the salt, an acid addition salt formed by a pharmaceutically acceptable free acid is useful. Acid addition salts are prepared by conventional methods, for example, by dissolving the compound in an excess of an aqueous acid solution, and precipitating the salt using a water miscible organic solvent such as methanol, ethanol, acetone or acetonitrile. Equivalent amounts of the compound and acid or alcohol in water (eg, glycol monomethyl ether) can be heated and then the mixture is evaporated to dryness or the precipitated salt can be suction filtered. At this time, inorganic and organic acids can be used as the free acid, hydrochloric acid, hydrobromic acid, phosphoric acid, nitric acid, sulfuric acid, and tartaric acid can be used as the inorganic acid, and as the organic acid, methane sulfonic acid, p-toluene sulfonic acid, acetic acid, Trifluoroacetic acid, maleic acid, succinic acid, oxalic acid, benzoic acid, tartaric acid, fumaric acid, manderic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid, and the like can be used, but are not limited thereto.

Also, bases can be used to make pharmaceutically acceptable metal salts. The alkali metal or alkaline earth metal salt is obtained, for example, by dissolving the compound in an excess of an alkali metal hydroxide or alkaline earth metal hydroxide solution, filtering the insoluble compound salt, and then evaporating and drying the filtrate. At this time, as the metal salt, it is particularly suitable to manufacture sodium, potassium, or calcium salts, but is not limited thereto. Further, the corresponding silver salt can be obtained by reacting an alkali metal or alkaline earth metal salt with a suitable silver salt (eg, silver nitrate).

The pharmaceutically acceptable salts of the compounds of Formulas 1 to 16, unless otherwise stated, include almost all salts of acidic or basic groups that may be present in the compounds. For example, pharmaceutically acceptable salts may include sodium, calcium and potassium salts of hydroxy groups, and other pharmaceutically acceptable salts of amino groups include hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts, and may be prepared by a method for preparing a salt known in the art.

The pharmaceutical composition comprising the diterpene of the present invention, or a pharmaceutically acceptable salt thereof, may be provided for the prevention or treatment of neurodegenerative diseases. Specifically, the neurodegenerative diseases may be any one selected from the group consisting of Parkinson's disease (PD), Alzheimer's disease (AD), amyotrophic lateral sclerosis (ALS), Huntington's disease (HD), Fronto-Temporal Dementia, Cortico Basal Degeneration, and Progressive supranuclear palsy (PSP).

According to one embodiment of the present invention, the compounds of Formulas 1 to 16 increased Nurr1 activity (Tables 2 and FIG. 2), and inhibited the nitric oxide production in microglia cells (Table 4). Specifically, the compounds of Formulas 2 and 8 show a better effect of increasing Nurr1 activity, and more specifically, Formula 2 shows not only an effect of increasing Nurr1 activity, but also a superior inhibition activity on nitric oxide production.

Also, the compounds of Formulas 11 to 16 increase Nurr1 activity (Table 3), inhibit the nitric oxide production e in microglia cells (Table 5), and inhibit the production of proinflammatory cytokines in microglia cells (FIGS. 1A-1D). Specifically, the compounds of Formulas 13, 14, and 16 show a better effect of increasing Nurr1 activity, and more specifically, Formula 14 shows not only an effect of increasing Nurr1 activity, but also a better inhibition activity on nitric oxide production.

Accordingly, a pharmaceutical composition comprising any one or more compounds selected from the group comprising the compounds of Formulas 1 to 16 of the present invention, or salts thereof, may be useful for the prevention or treatment of neurodegenerative diseases, wherein the compound included in the pharmaceutical composition may be any one or more compounds of Formulas 1 to 16.

As used herein, the term "treatment" refers to clinically intervening to alter the natural course of the individual or cell to be treated, which can be performed during or to prevent a clinical pathological condition. The desired therapeutic effects include preventing the occurrence or recurrence of the disease, alleviating symptoms, reducing all direct or indirect pathological consequences of the disease, reducing the rate of disease progression, alleviating or temporarily alleviating the disease state, relieving or improving prognosis. Preferably, the present invention includes all actions to improve the course of neurodegenerative diseases by administration of a composition comprising a diterpene, or a pharmaceutically acceptable salt thereof. Also, "prevention" refers to all actions to suppress or delay the development of the neurodegenerative disease by administration of a composition comprising a diterpene according to the present invention, or a pharmaceutically acceptable salt thereof.

The pharmaceutical composition of the present invention may further include a pharmaceutically acceptable carrier in addition to the diterpene or a pharmaceutically acceptable salt thereof as an active ingredient.

The type of carrier that can be used in the present invention is not particularly limited, and any carrier conventionally used in the art may be used. Non-limiting examples of the carrier can include saline, sterile water, Ringer's solution, buffered saline, albumin injection solution, lactose, dextrose, sucrose, sorbitol, mannitol, xylitol, erythritol, maltitol, maltodextrin, glycerol, ethanol, and the like. These may be used alone or in combination of 2 or more.

In addition, the pharmaceutical composition of the present invention can be used by adding other pharmaceutically acceptable additives, such as excipients, diluents, antioxidants, buffers or bacteriostatic agents, if necessary, and may be used by additionally adding a filler, a bulking agent, a wetting agent, a disintegrating agent, a dispersing agent, a surfactant, a binder, or a lubricant.

In the pharmaceutical composition of the present invention, the diterpene, or a pharmaceutically acceptable salt thereof, may be included in an amount of 0.01 to 90.00% by weight based on the total weight of the pharmaceutical composition, preferably 0.01% to 90.00% by weight, more preferably 0.1% to 70% by weight, much more preferably 0.1% to 50% by weight, but is not limited thereto, and may be variously changed according to a state of administration, a specific type of condition, and progression. If necessary, it may also be included in the total content of the pharmaceutical composition.

The pharmaceutical composition of the present invention is suitable for oral administration or parenteral administration and can be used in various formulations.

Non-limiting examples of formulations for oral administration using the pharmaceutical composition of the present invention include troches, lozenges, tablets, aqueous suspensions, oily suspensions, preparation powders, granules, emulsions, hard capsules, soft capsules, syrups or elixirs.

In order to formulate the pharmaceutical composition of the present invention for oral administration, binders such as lactose, saccharose, sorbitol, mannitol, starch, amylopectin, cellulose or gelatin, etc.; excipients such as dicalcium phosphate; disintegrants such as corn starch or sweet potato starch; lubricants such as magnesium stearate, calcium stearate, sodium stearyl fumarate or polyethylene glycol wax, etc. and sweetener, fragrance, syrup, etc. may also be used. Furthermore, in the case of capsules, in addition to the above-mentioned substances, a liquid carrier such as fatty oil may be additionally used.

Non-limiting examples of parenteral preparations using the pharmaceutical composition of the present invention include injection solutions, suppositories, respiratory inhalation powders, spray aerosols, ointments, application powders, oils, creams, and the like.

In order to formulate the pharmaceutical composition of the present invention for parenteral administration, sterilized aqueous solutions, non-aqueous solvents, suspensions, emulsions, freeze-dried preparations, external preparations, etc. may be used, wherein the non-aqueous solvent and suspension can be propylene glycol, polyethylene glycol, vegetable oil such as olive oil, and injectable ester such as ethyl oleate.

When the pharmaceutical composition of the present invention is formulated as an injectable solution, the pharmaceutical composition of the present invention is mixed in water with a stabilizer or a buffer to prepare a solution or suspension, which can be formulated for unit administration of ampoules or vials.

When the pharmaceutical composition of the present invention is formulated as an aerosol agent, a propellant or the like may be combined with an additive so that the dispersed concentrate or wet powder is dispersed.

When the pharmaceutical composition of the present invention is formulated with ointment, cream, powder for application, oil, external preparation for skin, etc., animal oil, vegetable oil, wax, paraffin, starch, trakant, cellulose derivative, polyethylene glycol, silicone, bentonite, Silica, talc, zinc oxide and the like can be used as a carrier.

The pharmaceutically effective amount and effective dose of the pharmaceutical composition of the present invention may be varied by the formulation method of the pharmaceutical composition, the administration mode, the administration time and/or the route of administration, and the type and extent of the reaction to be achieved by the administration of the pharmaceutical composition, the type of the subject to be administered, the age, weight, general health condition, the symptom or severity of the disease, sex, diet, excretion, the components of the drug or other composition used concurrently or separately with the subject and similar factors well known in the pharmaceutical field, and those skilled in the art can easily determine and prescribe a dose effective for the desired treatment.

The pharmaceutical composition of the present invention may be administered once a day, or may be divided into several times. The pharmaceutical composition of the present invention may be administered as an individual therapeutic agent or in combination with other therapeutic agents, and may be administered sequentially or simultaneously with conventional therapeutic agents. Considering all of the above factors, it can be administered in an amount that can obtain the maximum effect in a minimal amount without side effects, which can be easily determined by those skilled in the art.

"Pharmaceutically effective amount" for treatment means an amount sufficient to suppress or alleviate the disease in a reasonable ratio applicable to medical use, and the effective dose level can be decided by the type of subject, severity, age, sex, drug activity, drug sensitivity, the administration time and/or the route of administration and rate of release, duration of treatment, factors including concurrently used drugs, and other factors well known in the medical field. The composition of the present invention may be administered as an individual therapeutic agent or in combination with other therapeutic agents, and may be administered sequentially or simultaneously with conventional therapeutic agents. And it can be administered single or multiple.

Considering all of the above factors, it is important to administer an amount that can achieve the maximum effect in a minimal amount without side effects, and can be easily determined by those skilled in the art. For example, a pharmaceutically effective amount is 0.01 mg/day/kg body weight to 100 mg/day/kg body weight, specifically 0.1 mg/day/kg body weight to 10 mg/day/kg body weight to diterpene, or a pharmaceutically acceptable salt thereof.

The route of administration and the mode of administration of the pharmaceutical composition of the present invention may be independent of each other, and as long as the pharmaceutical composition can reach the target site of interest, any route of administration and mode of administration can be followed without particular limitation. The pharmaceutical composition may be administered by oral administration or parenteral administration.

As a method for parenteral administration of the pharmaceutical composition of the present invention, intravenous administration, intraperitoneal administration, intramuscular administration, transdermal administration or subcutaneous administration may be used, and a method of applying the composition to the diseased area, spraying, or inhaling may also be used, but is not limited thereto.

The pharmaceutical composition of the present invention may exhibit excellent effects even when used alone, but may be used in combination with various cancer treatment methods such as radiation therapy and chemotherapy to increase the treatment efficiency.

As another aspect of the present invention, the present invention is a pharmaceutical composition for the prevention or treatment of diseases caused by a Nurr1 dysfunction comprising a diterpene, or a pharmaceutically acceptable salt thereof, wherein the diterpene provides a pharmaceutical composition for the prevention or treatment of neurodegenerative diseases, at least one selected from the group comprising Formulas 1 to 16.

The term "Nurr1 (nuclear receptor related 1)" in the present invention refers to nuclear receptor-related 1 protein, also known as NR4A2 (nuclear receptor subfamily [0037] 4, group A, member 2), which is known to be encoded by the human NR4A2 gene, and it is also known to be involved in many neurodegenerative diseases, Although Nurr1 is an orphan nuclear receptor whose ligand has not yet been clearly identified, but Nurr1 is a protein belonging to the nuclear receptor family of intracellular transcription factors, and it was identified that Nurr1 plays a key role in maintaining the dopaminergic system in the brain. The disease caused by Nurr1 dysfunction is not limited thereto, but include neurodegenerative diseases such as Parkinson's disease (PD). Alzheimer's disease (AD), amyotrophic lateral sclerosis (ALS), Huntington's disease (HD), and Fronto-Temporal Dementia, Cortico Basal Degeneration, and Progressive supranuclear palsy (PSP) and a wide range of inflammatory diseases such as rheumatoid arthritis, schizophrenia, and bipolar disorder caused by dopamine dysfunction, As another aspect of the present invention, as a dietary supplement for preventing or improving neurodegenerative diseases comprising a diterpene, or a pharmaceutically acceptable salt thereof, the diterpene provides a health functional food for preventing or improving neurodegenerative diseases, which is at least one selected from the group containing Formulas 1 to 16.

The health functional food is a food that emphasizes the bio-regulatory function of food, and is a food that adds added value to act and express a specific purpose using physical, biochemical, and biotechnological methods. The components of these health functional foods are designed and processed to sufficiently exert the body control functions related to the body's defense and control of body rhythm, and prevention and recovery of diseases, and may contain food supplementary additives, sweeteners, or functional ingredients acceptable as food.

When using the diterpene of the present invention, or a pharmaceutically acceptable salt thereof, as a health functional food (or health functional beverage additive), the compound is added as it is or used with other foods or food ingredients, and may be suitably used according to conventional methods. The mixing amount of the compound may be appropriately determined according to its purpose of use (prevention, health or improvement, therapeutic treatment).

The health functional food may contain various nutrients, vitamins, minerals (electrolytes), flavoring agents such as synthetic flavors and natural flavors, colorants and enhancers (cheese, chocolate, etc.), pectic acid and salts thereof, organic acids, protective colloidal thickeners, pH adjusters, stabilizers, preservatives, glycerin, alcohol, carbonic acid used in carbonated drinks, and the like. Also, the health functional food of the present invention may contain flesh for the production of fruit and vegetable beverages. These ingredients may be used alone or in combination, and the proportion of these additives is generally selected from 0.001 to 50 parts by weight per total weight of the composition.

There are no particular restrictions on the type of the health functional food. Foods to which the compound can be added include sausage, meat, bread, chocolates, snacks, candy, confectionery, ramen, pizza, other noodles, gums, dairy products including ice cream, various soups, drinks, tea, alcoholic beverages and vitamin complexes, and the like. When formulated as a beverage, liquid components added in addition to new lactic acid bacteria are not limited thereto, but as with ordinary beverages, various flavoring agents or natural carbohydrates, and the like may be included as additional components.

The natural carbohydrate include monosaccharides (for example, glucose and fructose), disaccharides (for example, maltose and sucrose), polysaccharides (for example, dextrin, common sugars such as cycodextrin, etc), or xylitol, sorbitol, sugar alcohol such as erythritol, etc.

The present invention provides a method for treating neurodegenerative diseases, comprising a step administering to a subject a pharmaceutical composition comprising a diterpene or a pharmaceutically acceptable salt thereof as an active ingredient.

In the present invention, the subject refers to all animals, including humans, who have or develop neurodegenerative diseases, and may be subjects other than humans. By administering the pharmaceutical composition of the present invention to a subject, it shows an excellent effect in the treatment of neurodegenerative diseases.

The present invention provides the use of a composition comprising a diterpene, or a pharmaceutically acceptable salt thereof, in the manufacture of a medicament for the treatment of neurodegenerative diseases.

The present invention provides a composition comprising a diterpene, or a pharmaceutically acceptable salt thereof, for use in the treatment of neurodegenerative diseases.

Effects of the Invention

The diterpene of the present invention improves Nurr1 activity and exhibits an effect of inhibiting an inflammatory response in neurons, thereby it can be effectively used for the prevention or treatment of neurodegenerative diseases including Parkinson's disease caused by inhibition of Nurr1 activity.

BRIEF DESCRIPTION OF THE DRAWINGS

FIGS. 1A-1D show that compounds 11 to 16 of the present invention inhibit the expression of inflammation-related factors in BV-2 cells, which are microglia cells;

FIG. 1A shows that the inhibition of IL-1b expression was confirmed by Western blotting.

FIG. 1B is a graph confirming that the inhibition of IL-1b mRNA expression through PCR.

FIG. 1C is a graph confirming the inhibition of IL-6 mRNA expression through PCR.

FIG. 1D is a graph confirming through the PCR that inhibit the mRNA expression of TNF-a.

FIG. 2 is a graph confirming the effect of the compounds 1 to 10 of the present invention on Nurr1 activity

DETAILED DESCRIPTION

Hereinafter, the present invention will be described in more detail with reference to examples. However, these examples are for illustrative purposes only, and the scope of the present invention is not limited to these examples.

Example 1-a: Preparation of the Extract of *Daphne genkwa*

4.47 kg of dried flowers of *Daphne genkwa* were immersed in 40 L 80% ethanol for 72 hours, and filtered to obtain a liquid component. The obtained liquid component was concentrated under reduced pressure, and then 435 g of the extract of flower of *Daphne genkwa* was prepared.

Example 1-b 4.47 kg of the stem and root of *Daphne genkwa* were chopped, and then immersed in 12 L 80% ethanol for 4 hours, filtered to separate the solids and a first liquid component. The separated solid was again immersed in 12 L 80% ethanol for 4 hours, and filtered to obtain a second liquid component. The first liquid component and the second liquid component were mixed, the mixture was concentrated under reduced pressure, and the residue was lyophilized to prepare 255.1 g of extract of *Daphne genkwa*.

Example 2: Separation of Active Ingredient by Various Solvents from the Extract of *Daphne genkwa*

The extract of the flower of *Daphne genkwa* obtained in Example 1-a was sequentially fractionated with 2 L of distilled water and 2 L of hexane, chloroform, ethyl acetate, and butanol, respectively. The chloroform layer was concentrated under reduced pressure, and the chloroform fraction (17.6 g) was eluted with a gradient mixed solvent (100:0, 50:1, 20:1, 10:1, 5:1, 2:1, 1:1) of chloroform and methanol with silica gel column chromatography to obtain a total of 3 fractions (Fr. C1, C2, C3). Fr. C2 (4.5 g) was subjected to ODS silica gel chromatography with the gradient mixed solvent (60:40, 80:20, 100:0) of methanol and water to obtain 5 sub-fractions (Fr. C21, C22, C23, C24, C25). Fr. C23 (300 mg) was again subjected to silica gel (40-63 µm; 4 g flash column) MPLC on a gradient mixed solvent of chloroform and acetone (99:1-95:5) to obtain 3 sub-fractions (Fr. C231, C232, C233). Fr. C233 (140 mg) was finally subjected to ODS HPLC with 55% acetonitrile at a flow rate of 5 mL/min to obtain yuanhuafine (25.5 mg, compound of Formula 1) in the form of a white powder. The structure of the compound was identified based on the following NMR, MS, and $[\alpha]^{20}_D$ data.

[Formula 1]

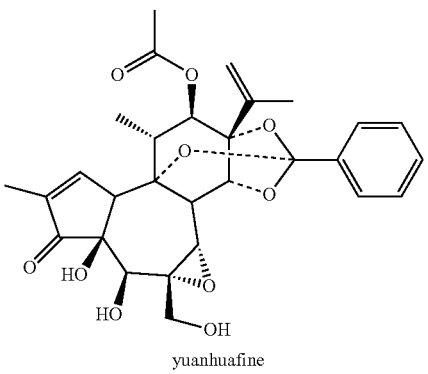

yuanhuafine $[\alpha]^{20}{}_D$ +29.3 (c 0.5, CHCl$_3$);
ESI-MS, m/z 573.9 [M+Na]$^+$;
$^1$H NMR values in ppm (CD$_3$OD, 400 MHz): $\delta_H$ 7.68 (dd, J=7.3, 1.8, 2H, H-3', H-7'), 7.57 (s, 1H, H-1'), 7.41-7.37 (m, 3H, H-4', H-5', H-6'), 5.08 (br, 1H, H-12), 5.05 (s, 1H, H-16a), 5.02 (d, J=2.4, 1H, H-16b), 4.98 (br, 1H, H-14), 4.14 (s, 1H, H-5), 4.05 (d, J=12.3, 1H, H-20a), 3.96 (m, 1H, H-10), 3.65 (dd, J=7.3, 4.9, 1H, H-20b), 3.59 (s, 1H, H-8), 2.54 (q, J=7.3, 1H, H-11), 2.00 (s, 3H, H-2''), 1.86 (s, 3H, H-17), 1.76 (d, J=1.1, 3H, H-19), 1.32 (d, J=7.3, 3H, H-18);
$^{13}$C NMR values in ppm (CD$_3$OD, 101 Hz): $\delta_C$ 209.8 (C-3), 171.6 (C-1''), 160.0 (C-1), 145.0 (C-15), 138.3 (C-2), 137.2 (C-2'), 130.5 (C-5'), 128.9 (C-4', C-6'), 127.2 (C-3', C-7'), 119.1 (C-1'), 113.9 (C-16), 85.4 (C-13), 82.1 (C-14), 80.3 (C-9), 79.8 (C-12), 74.5 (C-4), 71.3 (C-5), 65.1 (C-20), 64.7 (C-7), 63.2 (C-6), 48.9 (C-10), 45.1 (C-11), 36.6 (C-8), 21.0 (C-2''), 19.1 (C-18), 18.7 (C-17), 10.0 (C-19).

Fr. C24 (210 mg) was again subjected to Sephadex LH-20 column chromatography with a mixed solvent of chloroform and methanol (1:1), and was finally subjected to ODS HPLC with a 65% acetonitrile at a flow rate of 5 mL/min to obtain genkwadaphnine (25.0 mg, compound of Formula 2) in the form of a white powder. The structure of the compound was identified based on the following NMR, MS, and [ ]$^{20}{}_D$ data.

[Formula 2]

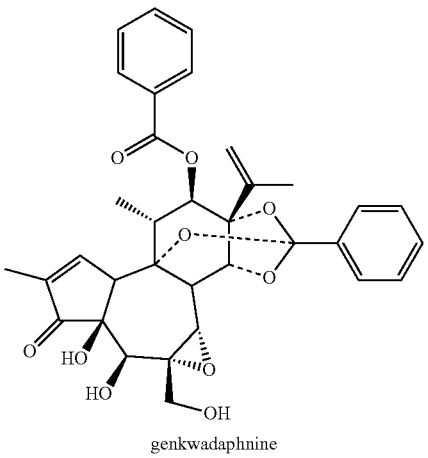

genkwadaphnine $[\alpha]^{20}{}_D$ +56.7 (c 0.1, CHCl$_3$);
ESI-MS, m/z 625.5 [M+Na]$^+$;
$^1$H NMR values in ppm (CD$_3$OD, 400 MHz); $\delta_H$ 7.98 (d, J=7.5, 2H, H-3'', H-7''), 7.72 (m, 2H, H-3', H-7'), 7.61 (m, 1H, H-5''), 7.59 (s, 1H, H-1), 7.48 (t, J=7.7, 2H, H-4'', H-6''), 7.40 (m, 3H, H-4', H-5', H-6'), 5.26 (br, 1H, H-12), 5.21 (d, J=2.4, 1H, H-14), 5.13 (s, 1H, H-16a), 5.02 (s, 1H, H-16b), 4.13 (s, 1H, H-5), 4.06 (d, J=12.3, 1H, H-20a), 3.99 (m, 1H, H-10), 3.76 (d, J=2.3, 1H, H-8), 3.68 (s, 1H, H-7), 3.66 (d, J=12.5, 1H, H-20b), 2.69 (q, J=7.3, 1H, H-11), 1.90 (s, 3H, H-17), 1.75 (s, 3H, H-19), 1.42 (d, J=7.3, 3H, H-18);
$^{13}$C NMR values in ppm (CD$_3$OD, 101 Hz): $\delta_C$ 209.8 (C-3), 166.9 (C-1''), 160.0 (C-1), 144.9 (C-15), 138.2 (C-2), 137.2 (C-2'), 134.5 (C-5''), 131.1 (C-2''), 130.7 (C-3'', C-7''), 130.5 (C-5'), 129.7 (C-4'', C-6''), 128.9 (C-4', C-6'), 127.2 (C-3', C-7'), 119.1 (C-1'), 114.1 (C-16), 85.7 (C-13), 82.0 (C-14), 80.4 (C-9), 80.2 (C-12), 74.4 (C-4), 71.4 (C-5), 65.2 (C-20), 64.8 (C-7), 63.2 (C-6), 49.9 (C-10), 45.3 (C-11), 37.0 (C-8), 19.1 (C-17), 18.9 (C-18), 10.0 (C-19).

Fr. C25 (130 mg) was again subjected to Sephadex LH-20 column chromatography with a mixed solvent of chloroform and methanol (1:1), and was finally subjected to ODS HPLC with a 70% acetonitrile at a flow rate of 5 mL/min to obtain genkwanine H (4.0 mg, compound of Formula 3) and genkwanine M (4.0 mg, compound of Formula 4) in the form of a white powder. The structure of the compound was identified based on the following NMR, MS, and $[\alpha]^{20}{}_D$ data.

[Formula 3]

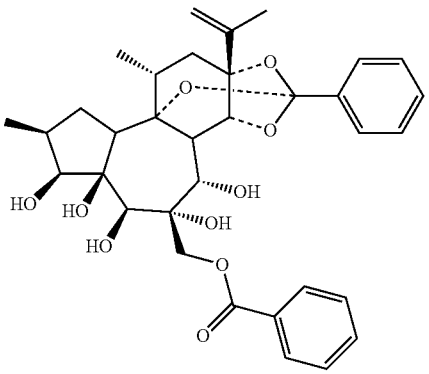

genkwanine H $[\alpha]^{20}{}_D$ +46.2 (c 1.5, CHCl$_3$);
ESI-MS, m/z 631.6 [M+Na]$^+$;
$^1$H NMR values in ppm (CD$_3$OD, 400 MHz): $\delta_H$ 8.09 (d, J=7.4, 2H, H-3'', H-7''), 7.67 (d, J=9.5, 2H, H-3', H-7'), 7.60 (t, J=7.4, 1H, H-5''), 7.49 (t, J=7.6, 2H, H-4'', H-6''), 7.36 (m, 3H, H-4', H-5', H-6'), 5.07 (s, 1H, H-16a), 4.91 (s, 1H, H-16 b), 4.78 (d, J=11.0, 1H, H-20a), 4.62 (d, J=2.5, 1H, H-14), 4.61 (s, 1H, H-7), 4.51 (d, J=11.1, 1H, H-20 b), 4.16 (d, J=4.1, 1H, H-2), 3.41 (s, 1H, H-5), 2.74 (m, 2H, H-10, H-11), 2.67 (d, J=2.3, 1H, H-8), 2.34 (dd, J=14.1, 8.0, 1H, H-12a), 1.84 (s, 3H, H-17), 1.81-1.65 (m, 4H, H-1, H-2, H-12 b), 1.31 (d, J=6.9, 3H, H-18), 1.06 (d, J=6.0, 3H, H-19);
$^1$H NMR values in ppm (CD$_3$OD, 176 Hz): $\delta_C$ 168.4 (C-1''), 148.3 (C-15), 137.9 (C-2'), 134.4 (C-5''), 131.8 (C-2''), 130.8 (C-3'', C-7''), 130.5 (C-5'), 129.7 (C-3', C-7'), 129.1 (C-4'', C-6''), 127.2 (C-4', C-6'), 118.6 (C-1'), 111.5 (C-16), 86.9 (C-13), 86.6 (C-14), 85.6 (C-9), 82.7 (C-4), 78.9 (C-3), 77.6 (C-6), 77.2 (C-7), 74.8 (C-5), 68.9 (C-20), 52.9 (C-10), 38.4 (C-8), 37.5 (C-12), 37.4 (C-2), 36.5 (C-11), 36.1 (C-1), 21.5 (C-18), 19.6 (C-17), 13.8 (C-19).

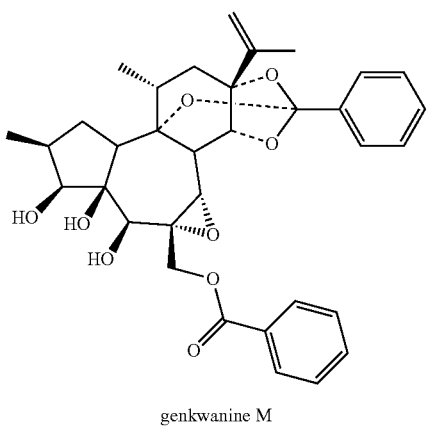

genkwanine M

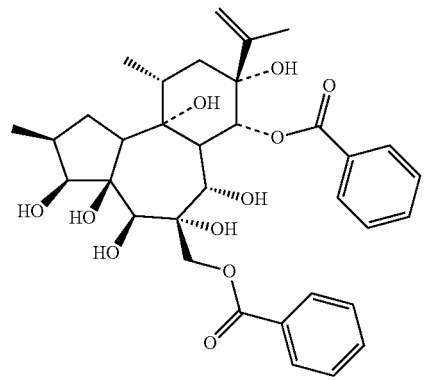

genkwanin K $[\alpha]^{20}_D$ -8.4 (c 0.05, MeOH);

ESI-MS, m/z 613.5 [M+Na]+;

1H NMR values in ppm (CD3OD, 400 MHz): δ$_H$ 8.07 (d, J=7.3, 2H, H-3", H-7"), 7.69 (d, J=9.5, 2H, H-3', H-7'), 7.61 (t, J=7.4, 1H, H-5"), 7.49 (t, J=7.7, 2H, H-4", H-6"), 7.35 (m, 3H, H-4', H-5', H-6'), 5.07 (s, 1H, H-16a), 5.06 (d, J=12.0, 1H, H-20a), 4.91 (s, 1H, H-16 b), 4.63 (d, J=2.6, 1H, H-14), 4.05 (d, J=11.8, 1H, H-20 b), 3.83 (s, 1H, H-3), 3.78 (s, 1H, H-5), 3.53 (s, 1H, H-7), 3.18 (d, J=2.6, 1H, H-8), 2.67 (t, J=9.0, 1H, H-10), 2.48 (m, 1H, H-11), 2.31 (dd, J=14.1, 8.0, 1H, H-12a), 1.84 (s, 3H, H-17), 1.79-1.55 (m, 4H, H-1, H-2, H-12 b), 1.27 (d, J=6.8, 3H, H-18), 1.04 (d, J=5.2, 3H, H-19);

13C NMR values in ppm (CD3OD, 176 Hz): δ$_C$ 168.0 (C-1"), 148.5 (C-15), 138.2 (C-2'), 134.4 (C-5"), 131.6 (C-2"), 130.8 (C-3", C-7"), 130.3 (C-5'), 129.74 (C-4", C-6"), 128.9 (C-3', C-7'), 127.4 (C-4', C-6'), 118.8 (C-1'), 111.4 (C-16), 86.1 (C-13), 84.0 (C-14), 82.2 (C-4), 81.1 (C-9), 78.8 (C-3), 73.4 (C-5), 69.3 (C-20), 65.8 (C-7), 62.0 (C-6), 50.3 (C-10), 38.4 (C-2), 38.0 (C-8), 37.2 (C-12), 36.6 (C-11), 36.1 (C-1), 21.6 (C-18), 19.6 (C-17), 13.7 (C-19).

Fr. C3 (4.0 g) was subjected to ODS silica gel chromatography with the gradient mixed solvent (60:40, 80:20, 100:0) of methanol and water to obtain 4 sub-fractions (Fr. C31, C32, C33, C34). Fr. C34 (1.06 g) was subjected to Sephadex LH-20 column chromatography with methanol to obtain 3 sub-fractions (Fr. C341, C342, C343). Fr. C341 (120 mg), C342 (180 mg), and C343 (119 mg) were finally subjected to ODS HPLC with 50% acetonitrile at a flow rate of 4.5 mL/min, respectively, to obtain genkwanin K (9.6 mg, compound of Formula 5) from Fr. C341, yuanhuapine (79.5 mg, compound of Formula 6) from Fr. C342, genkwanin A (4.7 mg, compound of Formula 7), orthobenzoate 2 (85.6 mg, compound of Formula 8), 1,2α-dihydrodaphnetoxin (2.9 mg, compound of Formula 9) and genkwanin I (2.4 mg, Formula 10 Compound) from Fr. C343 in the form of a white powder. The structure of the compound was identified based on the following NMR, MS, and $[\alpha]^{20}_D$ data.

$[\alpha]^{20}_D$ +38.5 (c 0.1, CHCl3);

ESI-MS, m/z 627.6 [M+Na]+;

1H NMR values in ppm (CD3OD, 400 MHz): δ$_H$ 7.98 (d, J=7.5, 2H, H-3', H-7'), 7.90 (d, J=7.5, 2H, H-3", H-7"), 7.57 (m, 2H, H-5', H-5"), 7.44 (d, J=7.7, 2H, H-4", H-6"), 7.42 (d, J=7.6, 2H, H-4', H-6'), 5.72 (d, J=6.2, 1H, H-14), 5.06 (s, 1H, H-16a), 4.84 (s, 1H, H-16 b), 4.62 (d, J=13.4, 1H, H-20a), 4.42 (d, J=3.0, 1H, H-3), 4.24 (d, J=5.15, 1H, H-20b), 4.19, (d, J=2.4, H-7), 3.33 (s, 1H, H-5), 3.15 (d, J=6.2, 1H, H-8), 2.34 (m, 2H, H-10, H-11), 2.01 (m, 3H, H-2, H-1a, H-12a), 1.81 (s, 3H, H-17), 1.60 (m, 2H, H-1b, H-12b), 1.24 (d, J=7.1, 3H, H-18), 1.08 (d, J=6.5, 3H, H-19);

1H NMR values in ppm (CDCl3, 101 Hz): δ$_C$ 168.3 (C-1"), 166.7 (C-1'), 148.1 (C-15), 133.6 (C-5"), 133.5 (C-5"'), 130.2 (C-3", C-7"), 130.1 (C-3', C-7'), 129.9 (C-2"), 129.4 (C-2'), 128.7 (C-4", C-6"), 128.6 (C-4', C-6'), 111.6 (C-16), 83.8 (C-4), 77.9 (C-9), 77.4 (C-6), 77.3 (C-14), 76.0 (C-7), 75.5 (C-3), 74.5 (C-13), 73.2 (C-5), 67.4 (C-20), 54.6 (C-10), 40.6 (C-8), 37.9 (C-12), 36.6 (C-2), 34.9 (C-1), 34.4 (C-11), 19.5 (C-18), 19.0 (C-17), 13.5 (C-19).

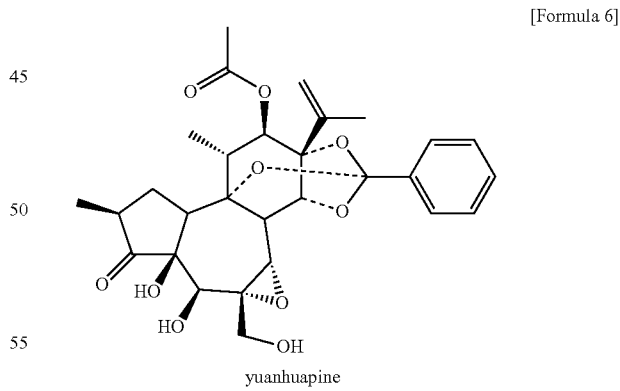

yuanhuapine $[\alpha]^{20}_D$ +28.5 (c 0.05, CHCl3);

ESI-MS, m/z 565.5 [M+Na]+;

1H NMR values in ppm (CD3OD, 400 MHz): δ$_H$ 7.67 (m, 2H, H-3', H-7'), 7.37 (m, 3H, H-4', H-5', H-6'), 5.07 (s, 1H, H-16a), 5.07 (d, J=2.9, 1H, H-12), 5.04 (s, 1H, H-16 b), 4.95 (d, J=2.7, 1H, H-14), 4.02 (s, 1H, H-5), 4.02 (d, J=12.1, 1H, H-20a), 3.61 (d, J=2.9, 1H, H-8), 3.60 (d, J=10.6, 1H, H-20 b), 3.54 (s, 1H, H-7), 3.18 (dd, J=13.3, 5.8, 1H, H-10), 2.47 (q, J=6.9, 1H, H-11), 2.38 (dt, J=13.3, 6.8, 1H, H-1a), 2.25

(dt, J=13.0, 6.6, 1H, H-1b), 2.01 (s, 3H, H-2"), 1.86 (s, 3H, H-17), 1.46 (d, J=13.1, 1H, H-2), 1.37 (d, J=7.0, 3H, H-18), 1.07 (d, J=6.5, 3H, H-19);

$^{13}$C NMR values in ppm (CD$_3$OD, 101 Hz): $\delta_C$ 218.9 (C-3), 171.6 (C-1"), 145.0 (C-15), 137.4 (C-2'), 130.4 (C-5'), 128.8 (C-4', C-6'), 127.1 (C-3', C-5'), 119.3 (C-1'), 113.7 (C-16), 84.8 (C-13), 82.3 (C-14), 80.6 (C-9), 79.2 (C-12), 77.0 (C-4), 70.5 (C-5), 65.3 (C-20), 64.6 (C-7), 63.3 (C-6), 44.9 (C-11), 44.8 (C-10), 43.7 (C-1), 36.8 (C-8), 34.5 (C-2), 21.1 (C-2"), 19.1 (C-18), 19.0 (C-17), 12.8 (C-19).

[Formula 7]

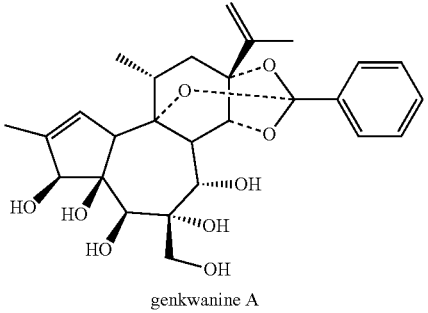

genkwanine A $[\alpha]^{20}_D$+47.7 (c 0.1, CHCl$_3$);
ESI-MS, m/z 505.6 [M+H]$^+$ and m/z 527.4 [M+Na]$^+$;

$^1$H NMR values in ppm (CD$_3$OD, 400 MHz): $\delta_H$ 7.66 (dd, J=6.6, 3.0, 2H, H-3', H-7'), 7.38 (m, 3H, H-4', H-5', H-6'), 5.07 (d, J=6.5, 1H, H-16a), 4.91 (s, 1H, H-16 b), 4.60 (d, J=2.5, 1H, H-14), 4.42 (s, 1H, H-7), 4.13 (d, J=4.6, 1H, H-3), 3.82 (q, J=11.0, 2H, H-20), 3.38 (s, 1H, H-5), 2.71 (m, 2H, H-10, H-11), 2.62 (d, J=2.4, 1H, H-8), 2.32 (dd, J=14.1, 8.0, 1H, H-12a), 1.87 (m, 2H, H-1a, H-2), 1.83 (s, 3H, H-17), 1.69 (m, 1H, H-1b), 1.62 (m, 2H, H-12b), 1.30 (d, J=6.9, 3H, H-18), 1.05 (d, J=6.2, 3H, H-19);

$^{13}$C NMR values in ppm (CD$_3$OD, 101 Hz): $\delta_C$ 148.3 (C-15), 137.9 (C-15), 130.6 (C-5'), 129.1 (C-4', C-6'), 127.3 (C-3', C-5'), 118.6 (C-1'), 111.5 (C-16), 86.8 (C-13), 86.5 (C-14), 85.4 (C-9), 82.8 (C-4), 78.5 (C-7), 78.3 (C-6), 77.5 (C-3), 75.0 (C-5), 67.6 (C-20), 52.9 (C-10), 38.5 (C-2), 37.5 (C-8), 37.4 (C-12), 36.5 (C-11), 36.0 (C-1), 21.5 (C-17), 19.8 (C-18), 13.8 (C-19).

[Formula 8]

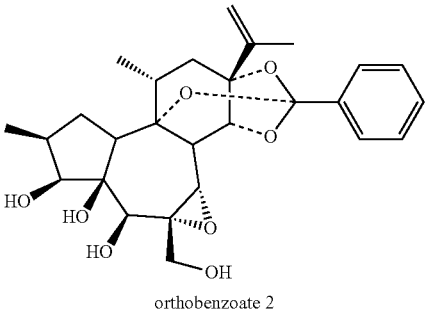

orthobenzoate 2

$[\alpha]^{20}_D$−16.6 (c 0.05, MeOH);
ESI-MS, m/z 509.2 [M+Na]$^+$;

$^1$H NMR values in ppm (CD$_3$OD, 400 MHz): $\delta_H$ 7.69 (dd, J=6.6, 2.9, 2H, H-3', H-7'), 7.35 (m, 3H, H-4', H-5', H-6'), 5.06 (s, 1H, H-16a), 4.90 (s, 1H, H-16b), 4.56 (d, J=2.6, 1H, H-14), 4.02 (d, J=12.2, 1H, H-20a), 3.76 (d, J=2.6, 1H, H-3), 3.70 (s, 1H, H-5), 3.59 (d, J=12.3, 1H, H-20 b), 3.42 (m, 1H, H-7), 3.07 (d, J=2.6, 1H, H-8), 2.67 (dd, J=12.6, 5.9, 1H, H-10), 2.47 (p, J=6.9, 1H, H-11), 2.28 (dd, J=13.9, 7.9, 1H, H-12a), 1.82 (s, 3H, H-17), 1.69 (d, J=14.0, 1H, H-1a), 1.64 (dd, J=9.5, 4.8, 1H, H-2), 1.58 (m, 2H, H-1b, H-12 b), 1.27 (d, J=6.8, 3H, H-18), 1.03 (d, J=5.3, 3H, H-19);

$^{13}$C NMR values in ppm (CD$_3$OD, 101 Hz): $\delta_C$ 148.3 (C-15), 138.1 (C-2'), 130.1 (C-5'), 128.7 (C-4', C-6'), 127.2 (C-3', C-7'), 118.5 (C-1'), 111.2 (C-16), 85.8 (C-13), 84.0 (C-14), 82.1 (C-9), 81.0 (C-2), 78.6 (C-4), 73.7 (C-5), 65.7 (C-20), 64.9 (C-7), 63.2 (C-6), 50.0 (C-10), 38.2 (C-2), 37.8 (C-8), 37.0 (C-12), 36.5 (C-11), 35.9 (C-1), 21.4 (C-17), 19.5 (C-18), 13.6 (C-19).

[Formula 9]

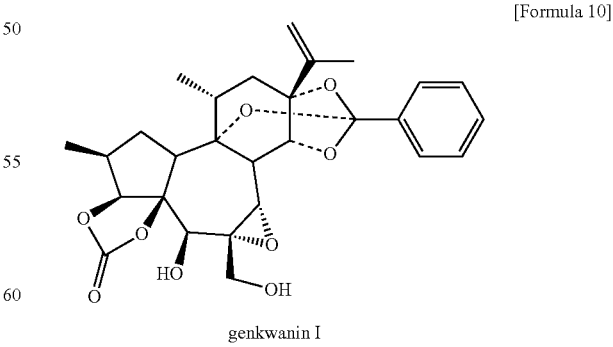

1, 2a -dihydrodaphnetoxin $[\alpha]^{20}_D$+6.2 (c 0.001, MeOH);
ESI-MS, m/z 507.3 [M+Na]$^+$;

$^1$H NMR values in ppm (CD$_3$OD, 400 MHz): $\delta_H$ 7.72 (m, 2H, H-3', H-7'), 7.36 (m, 3H, H-4', H-5', H-6'), 5.07 (s, 1H, H-16a), 4.91 (s, 1H, H-16b), 4.60 (d, J=2.8, 1H, H-14), 4.01 (s, 1H, H-5), 3.99 (d, J=12.2, 1H, H-20a), 3.57 (d, J=12.2, 1H, H-20 b), 3.44 (s, 1H, H-7), 3.16 (dd, J=13.3, 5.8, 1H, H-10), 3.01 (d, J=2.7, 1H, H-8), 2.55 (m, 1H, H-11), 2.38 (m, 1H, H-12a), 2.29 (m, 2H, H-1), 1.83 (s, 3H, H-17), 1.73 (d, J=14.0, 1H, H-2), 1.53 (m, 1H, H-12 b), 1.30 (d, J=6.8, 3H, H-18), 1.08 (d, J=6.6, 3H, H-19);

$^{13}$C NMR values in ppm (CD$_3$OD, 101 Hz): $\delta_C$ 219.3 (C-3), 148.3 (C-15), 138.1 (C-2'), 130.4 (C-5'), 128.9 (C-4', C-6'), 127.4 (C-3', C-5'), 118.8 (C-1'), 111.5 (C-16), 86.0 (C-13), 84.1 (C-14), 82.0 (C-9), 77.2 (C-4), 70.9 (C-5), 65.5 (C-20), 64.9 (C-7), 63.3 (C-6), 45.8 (C-10), 43.9 (C-8), 37.9 (C-1), 37.2 (C-2), 36.7 (C-12), 34.7 (C-11), 21.6 (C-17), 19.6 (C-18), 12.9 (C-19).

[Formula 10]

genkwanin I $[\alpha]^{20}_D$−22.8 (c 0.005, MeOH);
ESI-MS, m/z 513.3 [M+H]$^+$ and m/z 535.3 [M+Na]$^+$;

$^1$H NMR values in ppm (CD$_3$OD, 400 MHz): $\delta_H$ 7.69 (dd, J=7.5, 1.9, 2H, H-3', H-7'), 7.36 (m, 3H, H-4', H-5', H-6'), 5.09 (s, 1H, H-16a), 4.93 (s, 1H, H-16b), 4.72 (d, J=4.5, 1H, H-3), 4.64 (d, J=2.8, 1H, H-14), 4.10 (s, 1H, H-5), 4.09 (d, J=12.3, 1H, H-20a), 3.53 (d, J=12.4, 1H, H-20 b), 3.49 (s, 1H, H-7), 2.93 (dd, J=13.3, 6.1, 1H, H-10), 2.78 (d, J=2.8, 1H, H-8), 2.35 (dd, J=14.1, 7.8, 1H, H-12a), 2.12 (m, 1H, H-11), 2.04 (dd, J=11.7, 6.0, 1H, H-1a), 1.95 (dd, J=12.0, 6.6, 1H, H-2), 1.84 (s, 3H, H-17), 1.82 (d, J=14.9, 1H, H-12 b), 1.58 (d, J=12.6, 1H, H-1b), 1.31 (d, J=6.7, 3H, H-18), 1.13 (d, J=6.7, 3H, H-19);

$^{13}$C NMR values in ppm (CD$_3$OD, 101 Hz): $\delta_C$ 156.7 (C-21), 148.0 (C-15), 137.8 (C-2'), 130.5 (C-5'), 128.9 (C-4', C-6'), 127.4 (C-3', C-7'), 118.8 (C-1'), 111.8 (C-16), 94.1 (C-4), 90.4 (C-3), 85.8 (C-13), 84.2 (C-14), 81.4 (C-9), 71.1 (C-5), 65.0 (C-20), 64.7 (C-7), 62.8 (C-6), 50.7 (C-10), 37.9 (C-2), 37.4 (C-11), 37.3 (C-12), 37.1 (C-8), 36.2 (C-1), 21.6 (C-18), 19.5 (C-17), 12.9 (C-19).

Example 2-b: Separation of Active Ingredient by Various Solvents from *Daphne genkwa*

The extract of *Daphne genkwa* obtained in Example 1 was dissolved in a 1:1 mixed solvent of 200 mL of distilled water and hexane and fractionated to obtain a hexane layer. The hexane layer obtained by performing the same method twice more was concentrated under reduced pressure to obtain a hexane fraction. The obtained hexane fraction (20 g) is eluted with a gradient mixed solvent (10:1, 5:1, 2:1, 1:1, 1:2) of hexane and ethyl acetate with silica gel column chromatography to obtain a total of 3 fractions (Fr. I, II, III).

Fr. I (577 mg) was subjected to reverse phase silica gel prep TLC (75% acetonitrile) to obtain an active band. The active band was subjected to ODS HPLC with 83% acetonitrile at a flow rate of 3 mL/min, and acutilonine F (14.0 mg, compound of Formula 11) and wikstroemia factor M1 (7.0 mg, compound of Formula 12) were obtained in the form of a white powder at retention times of 15.2 minutes and 18.5 minutes, respectively. The structure of the compound was identified based on the following NMR, MS, and $[\alpha]^{20}_D$ data.

[Formula 11]

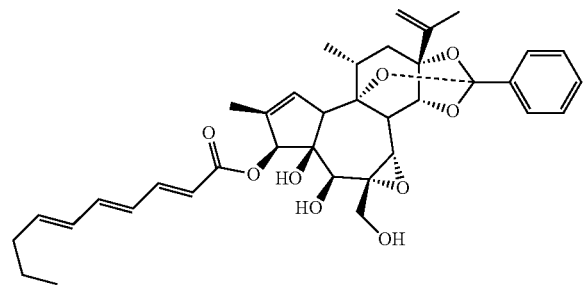

$[\alpha]^{20}_D$ −32.1 (c 1.3, MeOH);
ESI-MS, m/z 635.6 [M+H]$^+$, 657.7 [M+Na]$^+$;
$^1$H NMR (CD$_3$OD, 500 MHz): $\delta_H$, 7.70 (2H, dd, J=7.35, 2.22 Hz, H-3', H-7'), 7.37 (1H, m, H-5'), 7.36 (2H, m, H-4', H-6'), 7.35 (1H, m, H-3''), 6.64 (1H, dd, J=14.82, 10.75 Hz, H-5''), 6.34 (1H, dd, J=14.79, 11.40 Hz, H-4''), 6.22 (1H, dd, J=15.16, 10.69 Hz, H-6''), 6.01 (1H, m, H-7''), 6.00 (1H, m, H-2''), 5.06 (1H, brs, H-16a), 5.03 (1H, d, J=4.52 Hz, H-3), 4.90 (1H, brs, H-16 b), 4.56 (1H, d, J=2.66 Hz, H-14), 3.98 (1H, d, J=12.19 Hz, H-20a), 3.92 (1H, s, H-5), 3.59 (1H, d, J=12.20 Hz, H-20 b), 3.41 (1H, brs, H-7), 3.07 (1H, d, J=2.69 Hz, H-8), 2.83 (1H, dd, J=13.03, 5.32 Hz, H-10), 2.59 (1H, m, H-11), 2.29 (2H, m, H-12), 2.15 (2H, m, H-8''), 1.82 (3H, s, H-17), 1.78 (1H, m, H-2), 1.71 (2H, m, H-1), 1.47 (2H, m, H-9''), 1.31 (3H, d, J=6.89 Hz, H-18), 0.99 (3H, d, J=5.77 Hz, H-19), 0.94 (3H, t, J=7.39 Hz, H-10'');

$^{13}$C NMR values in ppm (CD$_3$OD, 126 Hz): $\delta_C$ 169.4 (C, C-1''), 148.5 (C, C-15), 147.2 (CH, C-3''), 143.3 (CH, C-5''), 141.9 (CH, C-7''), 138.2 (C, C-2'), 131.6 (CH, C-6''), 130.3 (CH, C-5'), 129.2 (CH, C-4''), 128.9 (CH, C-4', C-6'), 127.4 (CH, C-3', C-7'), 120.7 (CH, C-2''), 118.7 (C, C-1'), 111.4 (CH$_2$, C-16), 86.1 (C, C-13), 84.0 (CH, C-14), 82.9 (C, C-4), 82.3 (CH, C-3), 82.1 (C, C-9), 74.1 (CH, C-5), 66.1 (CH$_2$, C-20), 65.1 (CH, C-7), 63.0 (C, C-6), 37.9 (CH, C-8), 37.7 (CH, C-2), 37.3 (CH$_2$, C-1), 37.1 (CH$_2$, C-12), 36.5 (CH, C-11), 36.2 (CH$_2$, C-8''), 23.4 (CH$_2$, C-9''), 21.6 (CH$_3$, C-18), 19.6 (CH$_3$, C-17), 14.1 (CH$_3$, C-10''), 13.8 (CH$_3$, C-19).

[Formula 12]

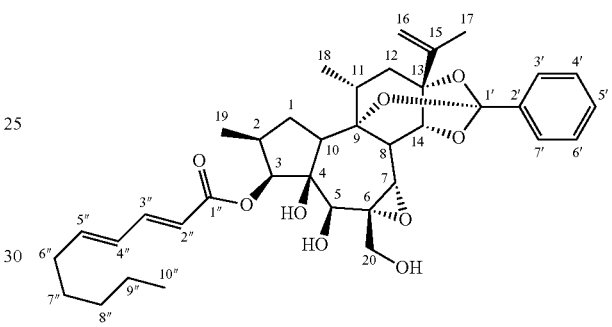

$[\alpha]^{20}_D$ +18.9 (c 1.0, MeOH);
ESI-MS, m/z 637.6 [M+H]$^+$, 659.4 [M+Na]$^+$, 635.2 [M−H]$^-$;
$^1$H NMR (CDCl$_3$, 500 MHz): $\delta_H$ 7.75 (2H, m, H-3', H-7'), 7.36 (3H, m, H-4', H-5', H-6'), 7.34 (1H, dd, J=15.4 and 10.2, H-3''), 6.21 (1H, dd, J=14.8 and 10.4, H-4''), 5.90 (1H, d, J=15.2, H-2''), 5.05 (1H, brs, H-16a), 4.92 (1H, brs, H-16b), 4.69 (1H, d, J=5.19, H-3), 4.51 (1H, d, J=2.76, H-14), 4.06 (1H, s, H-5), 3.88 (1H, d, J=12.2, H-20a), 3.77 (1H, d, J=12.2, H-20b), 3.44 (1H, s, H-7), 2.96 (1H, d, J=2.8, H-8), 2.82 (1H, dd, J=13.2, 5.5, H-10), 2.48 (1H, m, H-11), 2.20 (2H, overlapped, H-6''), 2.20 (1H, overlapped, H-12a), 1.93 (1H, m, H-1a), 1.83 (3H, s, H-17), 1.78 (1H, m, H-12b), 1.73 (1H, m, H-1b), 1.71 (1H, m, H-2), 1.45 (2H, m, H-7''), 1.33 (3H, d, J=6.9, H-18), 1.32 (2H, overlapped, H-9''), 1.31 (2H, overlapped, H-8''), 1.06 (3H, d, J=6.5, H-19), 0.91 (3H, t, J=6.9, H-10'');

$^{13}$C NMR (CDCl$_3$, 126 Hz): $\delta_C$ 169.6 (C, C-1''), 147.4 (CH, C-3''), 146.8 (CH, C-5''), 146.7 (C, C-15), 136.4 (C, C-2'), 129.4 (CH, C-5'), 128.4 (CH, C-4''), 128.2 (CH, C-4', C-6'), 126.3 (CH, C-3', C-7'), 118.0 (CH, C-2''), 117.6 (C, C-1'), 111.4 (CH$_2$, C-16), 84.5 (C, C-13), 82.7 (CH, C-14), 82.2 (CH, C-3), 81.7 (C, C-4), 80.5 (C, C-9), 75.0 (CH, C-5), 66.3 (CH$_2$, C-20), 64.2 (CH, C-7), 60.6 (C, C-6), 48.9 (CH, C-10), 36.6 (CH, C-8), 36.4 (CH, C-2), 36.3 (CH$_2$, C-12), 36.0 (CH$_2$, C-1), 35.5 (CH, C-11), 33.3 (CH$_2$, C-6''), 31.6 (CH$_2$, C-8''), 28.5 (CH$_2$, C-7''), 22.7 (CH$_2$, C-9''), 21.1 (CH$_3$, C-18), 19.4 (CH$_3$, C-17), 14.2 (CH$_3$, C-10''), 13.3 (CH$_3$, C-19).

Also, Fr. III (400 mg) was subjected to reverse phase silica gel prep TLC (75% acetonitrile) to obtain an active band. The active band was subjected to normal phase silica gel prep TLC (TLC) under CHCl3-MeOH (50:1) conditions to obtain Fr.III-1 and Fr.III-2 as 2 sub-fractions at Rf 0.4 and 0.25, respectively. Fr.III-1 was subjected to ODS HPLC with a 65% acetonitrile at a flow rate of 3 mL/min to obtain yuanhuadine (2.1 mg, compound of Formula 13) and yuanhuatine (4.0 mg, compound of Formula 14) in the form of a white powder at retention times of 17.2 min and 23.4 min, respectively. Fr.III-2 was subjected to ODS HPLC in the same manner as Fr.III-1, and to obtain prostratin Q (4.4 mg, compound of Formula 15) and 12-On-deca-2,4,6-trienoyl-phorbol-(13)-acetate (1.8 mg, compound of Formula 16) in the form of a white powder at retention times of 19.0 minutes and 21.4 minutes, respectively. The structure of the compound was identified based on the following NMR, MS, and $[\alpha]^{20}_D$ data.

[Formula 13]

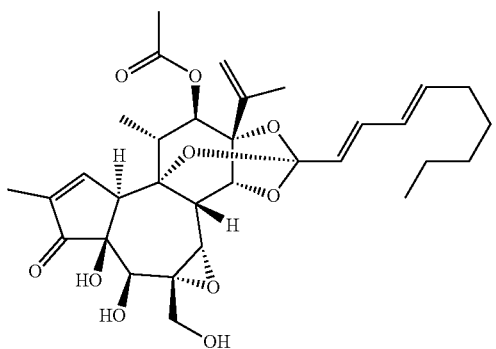

$[\alpha]^{20}_D$+14.1 (c 0.03, MeOH);

ESI-MS, m/z 579.5 [M+Na]$^+$;

$^1$HNM (CDCl$_3$, 500 MHz): $\delta_H$ 7.60 (1H, s, H-1), 7.24 (1H, m, H-3"), 6.19 (1H, m, H-4"), 6.15 (1H, m, H-5"), 5.79 (1H, d, J=15.41 Hz, H-2"), 5.70 (1H, d, J=4.71 Hz, H-7), 5.47 (1H, d, J=10.27 Hz, H-12), 4.03 (2H, q, J=13.04 Hz, H-20), 3.26 (2H, overlapped, H-8, H-10), 2.53 (2H, m, H-5), 2.17 (2H, overlapped, H-6"), 2.17 (1H, overlapped, H-11), 2.11 (3H, s, H-2'), 1.78 (3H, s, H-19), 1.44 (2H, m, H-7"), 1.32 (2H, m, H-9"), 1.31 (2H, m, H-8"), 1.27 (3H, s, H-16), 1.22 (3H, s, H-17), 1.10 (1H, d, J=5.20 Hz, H-14), 0.91 (3H, d, J=6.93 Hz, H-18), 0.90 (3H, t, J=7.06 Hz, H-10");

$^{13}$C NMR values in ppm (CDCl$_3$, 126 Hz); $\delta_C$ 209.1 (C, C-3), 174.1 (C, C-1'), 167.3 (C, C-1"), 161.0 (CH, C-1), 145.8 (CH, C-3"), 145.5 (CH, C-5"), 140.7 (C, C-6), 133.1 (C, C-2), 129.5 (CH, C-7), 128.5 (CH, C-4"), 119.1 (CH, C-2"), 78.4 (C, C-9), 74.0 (C, C-4), 68.2 (CH$_2$, C-20), 65.9 (C, C-13), 56.4 (CH, C-10), 43.4 (CH, C-11), 39.3 (CH, C-8), 38.9 (CH$_2$, C-5), 36.6 (CH, C-14), 33.2 (CH$_2$, C-6"), 31.6 (CH$_2$, C-8"), 28.6 (CH$_2$, C-7"), 25.9 (C, C-15), 24.0 (CH$_3$, C-17), 22.7 (CH$_2$, C-9"), 21.3 (CH$_3$, C-2'), 17.0 (CH$_3$, C-16), 14.2 (CH$_3$, C-10"), 10.3 (CH$_3$, C-19).

[Formula 14]

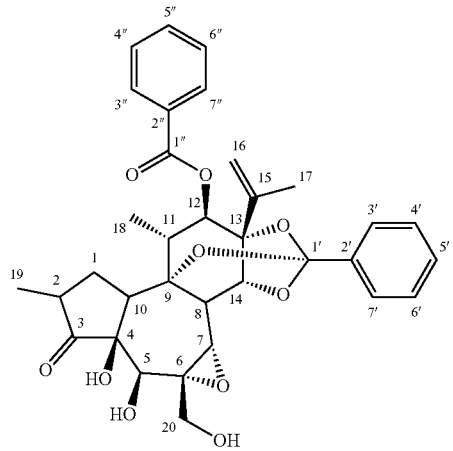

$[\alpha]^{20}_D$+7.5 (c 1.3, CH$_2$Cl$_2$);

ESI-MS, m/z 587.6 [M+H]$^+$ and 609.5 [M+Na]$^+$;

$^1$H NMR (CDCl$_3$, 500 MHz): $\delta_H$7.58 (1H, s, H-1), 6.67 (1H, dd, J=15.45, 10.66 Hz, H-3'), 6.05 (1H, dd, J=15.14, 10.71 Hz, H-4'), 5.86 (1H, m, H-5'), 5.65 (1H, d, J=15.46 Hz, H-2'), 5.02 (1H, brs, H-16a), 4.99 (1H, brs, H-12), 4.96 (1H, brs, H-16b), 4.76 (1H, d, J=2.47 Hz, H-14), 4.26 (1H, brs, H-7), 3.94 (1H, dd, J=12.34, 5.86 Hz, H-20a), 3.82 (1H, m, H-10), 3.80 (1H, m, H-20 b), 3.56 (1H, s, H-5), 3.52 (1H, d, J=2.45 Hz, H-8), 2.38 (1H, q, J=7.22 Hz, H-11), 2.10 (2H, q, J=7.20 Hz, H-6'), 2.00 (3H, s, H-2"), 1.84 (3H, s, H-17), 1.80 (3H, d, J=1.31 Hz, H-19), 1.39 (2H, dt, J=14.26, 7.28 Hz, H-7'), 1.30 (2H, m, H-9'), 1.27 (2H, m, H-8'), 0.89 (3H, t, J=6.93 Hz, H-10');

$^{13}$CNMR values in ppm (CDCl$_3$, 126 Hz): $\delta_C$ 209.7 (C, C-3), 169.9 (C, C-1"), 160.6 (CH, C-1), 143.3 (C, C-15), 139.6 (CH, C-5'), 137.1 (C, C-2), 135.3 (CH, C-3'), 128.8 (CH, C-4'), 122.5 (CH, C-2'), 117.2 (C, C-1'), 113.5 (CH$_2$, C-16), 83.9 (C, C-13), 80.7 (CH, C-14), 78.5 (CH, C-12), 78.3 (C, C-9), 72.5 (C, C-4), 72.2 (CH, C-5), 65.3 (CH$_2$, C-20), 64.5 (C-7), 60.7 (C-6), 47.7 (CH, C-10), 44.3 (CH, C-11), 35.6 (CH, C-8), 32.9 (CH$_2$, C-6'), 31.5 (CH$_2$, C-8'), 28.9 (CH$_2$, C-7'), 22.7 (CH$_2$, C-9'), 21.4 (CH$_3$, C-2"), 18.9 (CH$_3$, C-17), 18.5 (CH$_3$, C-18), 14.2 (CH$_3$, C-10'), 10.1 (CH$_3$, C-19).

[Formula 15]

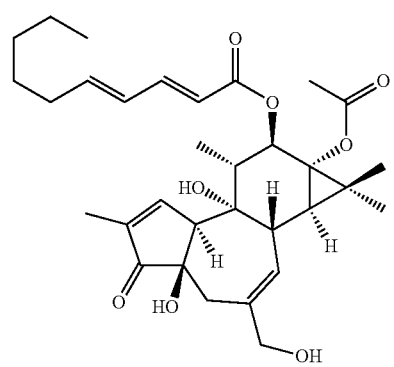

$[\alpha]^{20}_D$+52.8 (c 0.5, MeOH);

ESI-MS, m/z 605.5 [M+H]$^+$, 627.4 [M+Na]$^+$, 603.3 [M−H]$^-$;

¹HNMR (CDCl₃, 500 MHz): δ$_H$ 7.94 (2H, m, H-3", H-7"), 7.75 (2H, m, H-3', H-7'), 7.60 (1H, t, J=7.4, H-5"), 7.48 (2H, m, H-4", H-6"), 7.40 (3H, m, H-4', H-5', H-6'), 5.42 (1H, brs, H-12), 5.07 (1H, brs, H-16a), 5.03 (1H, brs, H-16 b), 4.99 (1H, d, J=2.8, H-14), 4.10 (1H, s, H-5), 3.90 (1H, d, J=12.4, H-20a), 3.85 (1H, d, J=12.3, H-20b), 3.69 (1H, d, J=2.8, H-8), 3.67 (1H, brs, H-7), 3.06 (1H, dd, J=13.3 and 5.9, H-10), 2.59 (1H, q, J=6.9, H-11), 2.40 (1H, m, H-1a), 2.28 (1H, m, H-2), 1.92 (3H, s, H-17), 1.63 (1H, m, H-1b), 1.51 (3H, d, J=6.9, H-18), 1.12 (3H, d, J=6.6, H-19);

¹³CNMR (CDCl₃, 126 Hz): δ$_C$ 220.4 (C, C-3), 165.8 (C, C-1"), 143.2 (C, C-15), 135.7 (C, C-2'), 133.5 (CH, C-5"), 130.0 (CH, C-5'), 129.8 (C, C-2"), 129.7 (CH, C-3", C-7"), 128.9 (CH, C-4", C-6"), 128.3 (CH, C-4', C-6'), 126.2 (CH, C-3', C-7'), 118.4 (C, C-1'), 113.8 (CH₂, C-16), 83.9 (C, C-13), 81.4 (CH, C-14), 79.3 (C, C-9), 78.7 (CH, C-12), 75.2 (C, C-4), 71.5 (CH, C-5), 65.3 (CH₂, C-20), 64.5 (CH, C-7), 61.0 (C, C-6), 44.3 (CH, C-11), 44.2 (CH, C-10), 43.1 (CH, C-2), 36.3 (CH, C-8), 33.6 (CH₂, C-1), 19.0 (CH₃, C-17, C-18), 12.6 (CH₃, C-19).

[Formula 16]

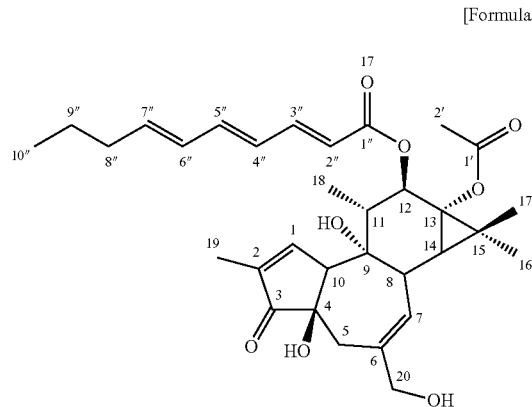

[α]²⁰$_D$–15.1 (c 0.2, CHCl₃);
ESI-MS, m/z 577.5 [M+Na]⁺, 553.4 [M–H]⁻;

¹HNMR (CDCl₃, 500 MHz): δ$_H$7.61 (1H, s, H-1), 7.28 (1H, dd, J=15.3 and 11.22, H-3"), 6.54 (1H, dd, J=14.9 and 10.7, H-5"), 6.23 (1H, dd, J=14.8 and 11.4, H-4"), 6.15 (1H, dd, J=15.1 and 10.8, H-6"), 5.95 (1H, m, H-7"), 5.84 (1H, d, J=15.3, H-2"), 5.70 (1H, d, J=4.8, H-7), 5.47 (1H, d, J=10.3, H-12), 4.05 (1H, d, J=12.9, H-20a), 4.00 (1H, d, J=12.9, H-20 b), 3.26 (1H, overlapped, H-10), 3.26 (1H, overlapped, H-8), 2.52 (2H, m, H-5), 2.17 (1H, m, H-11), 2.13 (2H, overlapped, H-8"), 2.11 (3H, s, H-2'), 1.78 (3H, d, J=1.5, H-19), 1.45 (2H, dq, J=14.6 and 7.3, H-9"), 1.27 (3H, s, H-16), 1.22 (3H, s, H-17), 1.10 (1H, d, J=5.1, H-14), 0.93 (3H, t, J=7.3, H-10"), 0.91 (3H, d, J=6.4, H-18);

¹³CNMR (CDCl₃, 126 Hz): δ$_C$ 209.2 (C, C-3), 174.1 (C, C-1'), 167.2 (C, C-1"), 161.0 (CH, C-1), 145.6 (CH, C-3"), 141.8 (CH, C-5"), 141.0 (CH, C-7"), 140.7 (C, C-6), 133.1 (C, C-2), 130.2 (CH, C-6"), 129.5 (CH, C-7), 127.9 (CH, C-4"), 119.9 (CH, C-2"), 78.5 (C, C-9), 76.9 (CH, C-12), 74.0 (C, C-4), 68.2 (CH₂, C-20), 65.9 (C, C-13), 56.4 (CH, C-10), 43.4 (CH, C-11), 39.3 (CH, C-8), 38.8 (CH₂, C-5), 36.6 (CH, C-14), 35.5 (CH₂, C-8"), 26.0 (C, C-15), 24.0 (CH₃, C-17), 22.4 (CH₂, C-9"), 21.3 (CH₃, C-2'), 17.0 (CH₃, C-16), 14.6 (CH₃, C-18), 13.9 (CH₃, C-10"), 10.3 (CH₃, C-19).

Example 3: Effect of Compounds on Nurr1 Activity

As in Example 2, Nurr1 activity according to the concentration of the diterpene isolated from the extract of *Daphne genkwa* was confirmed through luciferase analysis.

Specifically, after synthesizing a vector in which the gene having the nucleotide sequence (5'-CTCG-GAGGACAGTACTCCG-3 SEQ ID NO:1) to which the GLA4 gene can bind is repeated 8 times to the reporter gene, luciferase, is synthesized, 3 types of plasmid DNA, including DNA containing Nurr1-LBD and DNA with β-galactosidase, were transfected into BE(2)C cells. After 6 hours, the compounds 1 to 10 separated in Example 2 were treated according to the concentrations in Table 1 below. The cells thus treated were cultured in a 5% carbon dioxide incubator at 37° C. for 20 hours, and then luciferase analysis was performed. As a control, 0.1% DMSO was used, and at this time, the activity was increased by multiple, and Amodiaquine was used as a positive control.

TABLE 1

| compound | Final treatment concentration (μM) | | |
| --- | --- | --- | --- |
| | low | mid | high |
| AQ (Amodiaquine) | 5 | 20 | — |
| Formula 1 | 0.01 | 0.1 | 1 |
| Formula 2 | 0.01 | 0.1 | 1 |
| Formula 3 | 0.1 | 1 | 10 |
| Formula 4 | 0.1 | 1 | 10 |
| Formula 5 | 0.1 | 1 | 10 |
| Formula 6 | 0.01 | 0.1 | 1 |
| Formula 7 | 0.1 | 1 | 10 |
| Formula 8 | 0.1 | 1 | 10 |
| Formula 9 | 0.1 | 1 | 10 |
| Formula 10 | 1 | 10 | 100 |
| DG-2 (control) | 0.01 | 0.1 | 1 |

As a result of the analysis, as shown in Table 2 and FIG. 2, all compounds of Formulas 1 to 10 activated Nurr1. Specifically, all compounds of Formulas 1 to 10 activated Nurr1 when treated at a concentration of 1 μM, in particular, it was confirmed that the compound of Formula 2 has excellent effect of Nurr1 activity even at a low concentration of 0.01 μM. Thereby, it was found that the compounds isolated from the extract of *Daphne genkwa* activate Nurr1 and at the same time, Nurr1 activity may be different depending on the structure of the compound.

TABLE 2

| Conc. | DMSO | AQ | 1 | 2 | 3 | 4 | 5 | 6 | 7 | 8 | 9 | 10 | DGII-2 |
| --- | --- | --- | --- | --- | --- | --- | --- | --- | --- | --- | --- | --- | --- |
| Low | 1.0 | 0.9 | 1.0 | 2.1 | 1.2 | 1.0 | 0.9 | 1.0 | 1.2 | 1.7 | 1.7 | 1.8 | 1.1 |
| Midium | — | 1.8 | 1.5 | 2.2 | 1.4 | 1.4 | 1.2 | 1.8 | 2.6 | 2.0 | 2.4 | 1.9 | 2.6 |
| High | — | — | 1.7 | 1.9 | 1.4 | 1.7 | 1.9 | 2.4 | 2.0 | 1.6 | 1.5 | 1.1 | 2.2 |

As a result of the analysis, as shown in Table 3 below, compounds 13 and 14 activated Nurr1 even at a low concentration of 0.003 μM, and compound 16 in addition to compounds 13 and 14 significantly activates Nurr1 at 0.03 μM. Thereby, it was found that the compounds isolated from the extract of *Daphne genkwa* activated Nurr1 and Nurr1 activity could be different depending on the structure of the compound.

TABLE 3

| density (μM) | Positive control | compound 11 | compound 12 | compound 13 | compound 14 | compound 15 | compound 16 |
|---|---|---|---|---|---|---|---|
| 0.003 | — | — | — | 1.23 ± 0.09 | 1.03 ± 0.15 | — | — |
| 0.01 | — | — | — | 1.35 ± 0.28 | 0.94 ± 0.04 | — | — |
| 0.03 | — | 1.28 ± 0.18 | 1.4 ± 0.18 | *1.47 ± 0.17 | *1.63 ± 0.18 | 1.17 ± 0.22 | *1.42 ± 0.15 |
| 0.1 | — | 1.16 ± 0.16 | **1.29 ± 0.04 | *1.42 ± 0.14 | **1.68 ± 0.11 | 1.28 ± 0.35 | *1.68 ± 0.43 |
| 0.3 | — | 1.32 ± 0.13 | *1.33 ± 0.06 | *1.65 ± 0.2 | **1.62 ± 0.11 | **1.59 ± 0.08 | *1.82 ± 0.51 |
| 1 | 0.8 ± 0.03 | *1.76 ± 0.08 | *1.62 ± 0.21 | **1.47 ± 0.02 | *1.67 ± 0.32 | *2.12 ± 0.37 | **1.53 ± 0.07 |
| 5 | 1.1 ± 0.15 | — | — | — | — | — | — |
| 10 | **1.6 ± 0.03 | — | — | — | — | — | — |
| 20 | **2.7 ± 0.37 | — | — | — | — | — | — |

($*P < 0.05$, $**P < 0.01$ compared to control treatment)

Example 4: Inhibition Activity on Nitric Oxide Production in a Microglia BV-2 Cell The death of cranial nerve cells due to an inflammatory reaction in a microglia cell has been reported as one of the main causes of degenerative brain diseases such as dementia and Parkinson's disease. (Sarkar S et al., Neurotoxicology, 44, 250-262 (2014); Bower J H et al., Neurology, 67, 494-496 (2006)). Accordingly, the inhibition activity on nitric oxide production, a representative inflammatory factor, was investigated for the compounds isolated from Example 2 in a microglia. Specifically, microglia BV-2 cells were put into a 96-well plate at $5 \times 10^4$ cells/well, and cultured for 2 days, followed by incubation with LPS (1 mg/mL) for 24 hours with the compound isolated in Example 2 above. The culture supernatant was measured for absorbance at 540 nm using the Griess reagent to quantify nitrite to investigate the amount of nitric oxide production. Minocyline was used as a positive control.

As a result of the investigation, as shown in Tables 4 and 5 below, it was confirmed that all compounds inhibit nitric oxide production at a low concentration. In particular, it was confirmed that genkwadaphnine of compound 2 exhibits inhibition activity on nitric oxide production at a very low concentration of 0.06±0.02, and compound 14 exhibited inhibition activity of nitric oxide production at a very low concentration of 1.03 μM.

TABLE 4

| Compound | IC$_{50}$ (μM) |
|---|---|
| Minocycline | 21.28 ± 0.48 |
| Formula 1 (yuanhuafine) | 0.37 ± 0.15 |
| Formula 2 (genkwadaphnine) | 0.06 ± 0.02 |
| Formula 3 (genkwanine H) | 1.06 ± 0.12 |
| Formula 4 (genkwanine M) | 0.18 ± 0.04 |
| Formula 5 (genkwain K) | 4.67 ± 3.10 |
| Formula 6 (yuanhuapine) | 0.25 ± 0.06 |
| Formula 7 (genkwanin A) | 3.41 ± 0.99 |
| Formula 8 (orthobenzoate 2) | 1.22 ± 0.13 |
| Formula 9 (1,2 α-dihydrodaphnetoxin) | 1.60 ± 0.37 |
| Formula 10 (genkwanin I) | 7.79 ± 0.91 |

TABLE 5

| | Positive control | compound 11 | compound 12 | Compound 13 | compound 14 | compound 15 | compound 16 |
|---|---|---|---|---|---|---|---|
| IC$_{50}$ (μM) | 29.9 | 3.49 | 2.3 | 1.8 | 1.03 | 3.73 | 1.78 |

Example 5: Inhibition Activity of Pro-Inflammatory Cytokines Production in a Microglia BV-2 Cell The inhibition activity of compounds production against IL-1b, IL-6 and TNFa, which are representative inflammatory factors in microglia, was investigated. Microglia BV-2 cells were placed in a 96 well plate at $1 \times 10^5$ cells/well, and LPS (1 mg/mL) was incubated with the compound for 5 hours. Cells were recovered from each well and subjected to Western blotting and real-time PCR.

Specifically, the expression level of IL-1b was investigated by Western blotting. Rabbit anti-IL-1b [Cell Signaling (Danvers, MA, USA); 1:1000]) was used as the primary antibody, mouse anti-actin (Sigma 1:5000) was used as a control. As a secondary antibody, horseradish peroxidase-conjugated anti-mouse or anti-rabbit immunoglobulin G (IgG) antibody (Amersham, Piscataway, NY, USA) was used, and was observed by coloring with an enhanced-chemiluminescent substrate (Amersham).

In addition, mRNA expression levels of IL-1b, IL-6, and TNF-a were analyzed by real-time quantatitive PCR. Primers of all rat cytokines and GAPDH were purchased from Invitrogen, and the cytokine mRNA expression level was determined by normalizing to the GAPDH mRNA expression level.

As a result of Western blotting and PCR, as shown in FIGS. 1A and 1B, it was confirmed that the expression level of IL-1b decreased in the administration group of all compounds. In addition, as a result of PCR, as shown in FIGS. 1C and 1D, it was confirmed that the expression level of IL-6 and TNF-a also decreased in the administration group of all compounds.

In the present invention, the contents that can be sufficiently recognized and inferred by those of ordinary skill in the technical field of the present invention are omitted, and in addition to the specific examples described in the present invention, various modifications are possible within a range that does not change the technical spirit or essential configuration of the present invention. Therefore, the present invention may be implemented in a different manner from those specifically described and exemplified in this specification, which is understood by those skilled in the art of the present invention.

INDUSTRIAL AVAILABILITY

As described above, the present invention relates to a pharmaceutical composition for the prevention or treatment of neurodegenerative diseases comprising a diterpene, or a pharmaceutically acceptable salt thereof, by showing the effect of suppressing the inflammatory response in neurons, shows the effect of suppressing the inflammatory response in neurons, and can be usefully used for the prevention and treatment of neurodegenerative diseases including Parkinson's disease caused by the inhibition of Nurr1 activity.

```
[Sequence list free text]
DNA
Artificial Sequence
GLA4 binding gene
                                    SEQ ID NO: 1
ctcggaggac agtactccg
```

What is claimed is:

1. A method of treating a neurodegenerative disease comprising administering a pharmaceutical composition consisting of a pharmaceutically effective amount of one and only one isolated diterpene selected from the group consisting of Formulas 1 to 10, or a pharmaceutically acceptable salt thereof as an active ingredient and a pharmaceutically acceptable carrier, optionally with conventional therapeutic agents for treating neurodegenerative diseases to a subject in need thereof, wherein the composition excludes an extract of *Daphne genkwa*:

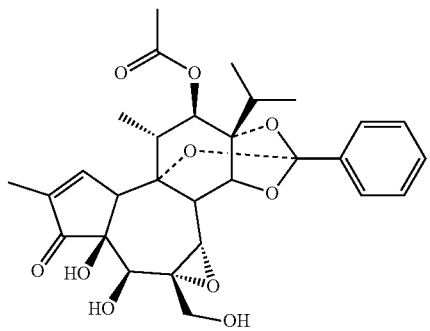

[Formula 1]

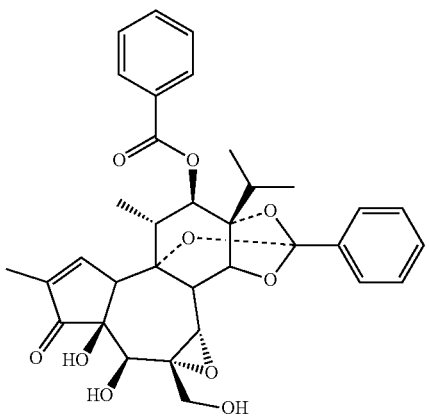

[Formula 2]

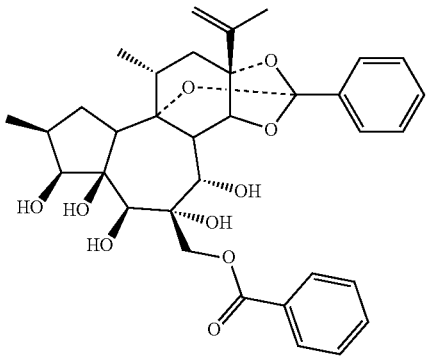

[Formula 3]

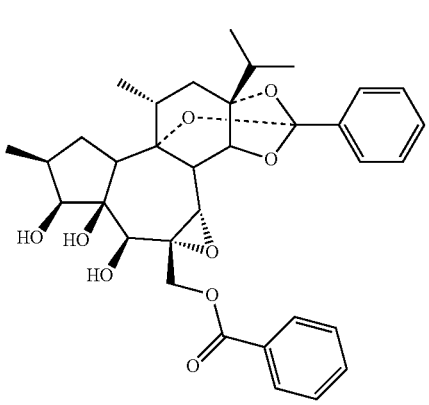

[Formula 4]

[Formula 5]

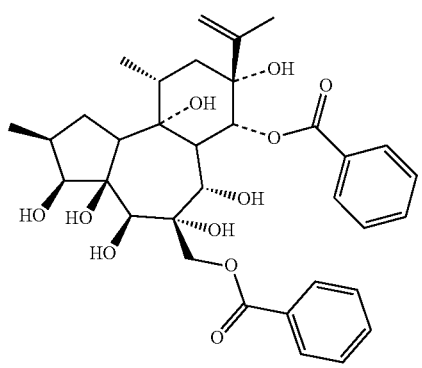

[Formula 6]

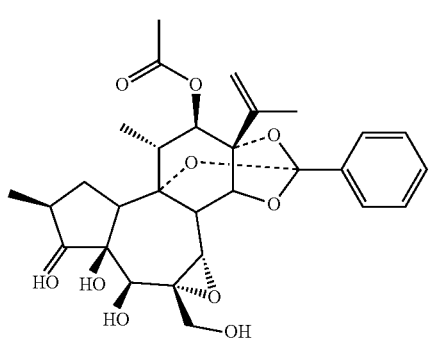

[Formula 7]

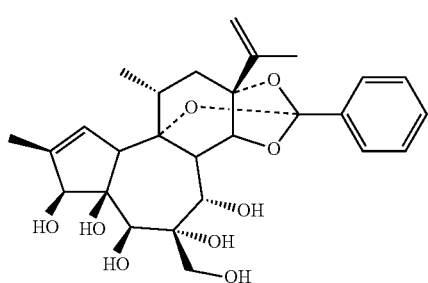

[Formula 8]

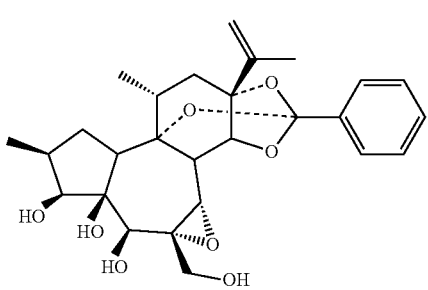

[Formula 9]

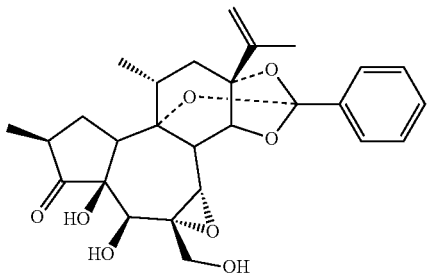

[Formula 10]

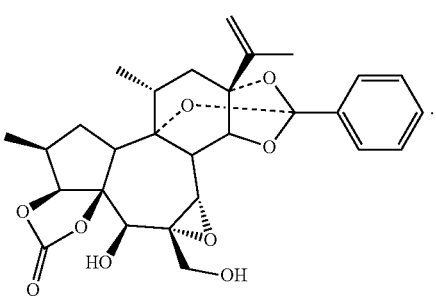

2. The method treatment of according to claim 1, wherein the diterpene is the compounds represented by Formula 2, or 8.

3. The method according to claim 1, wherein the diterpene is the compound represented by Formula 2.

4. The method according to claim 1, wherein the neurodegenerative disease is any one selected from the group consisting of Parkinson's disease (PD), Alzheimer's disease (AD), amyotrophic lateral sclerosis (ALS), Huntington's disease (HD), Fronto-Temporal Dementia, Cortico Basal Degeneration, and Progressive supranuclear palsy (PSP).

5. The method according to claim 1, wherein the neurodegenerative disease is Parkinson's disease (PD).

* * * * *